(12) United States Patent
Bishay et al.

(10) Patent No.: US 8,613,709 B2
(45) Date of Patent: Dec. 24, 2013

(54) AMBULATORY ELECTROCARDIOGRAPHIC MONITOR FOR PROVIDING EASE OF USE IN WOMEN

(75) Inventors: Jon Mikalson Bishay, Seattle, WA (US); Gust H. Bardy, Carnation, WA (US); Jason Felix, Vashon Island, WA (US)

(73) Assignee: Cardiac Science Corporation, Waukesha, WI (US)

( * ) Notice: Subject to any disclaimer, the term of this patent is extended or adjusted under 35 U.S.C. 154(b) by 215 days.

(21) Appl. No.: 13/191,414

(22) Filed: Jul. 26, 2011

(65) Prior Publication Data

US 2012/0088999 A1      Apr. 12, 2012

Related U.S. Application Data

(63) Continuation-in-part of application No. 12/901,428, filed on Oct. 8, 2010, now abandoned.

(51) Int. Cl.
*A61B 5/04* (2006.01)

(52) U.S. Cl.
USPC ............ 600/508; 600/382; 600/386; 600/509

(58) Field of Classification Search
USPC ......... 600/372, 382, 384, 386–388, 391–393, 600/508–509; 607/149, 152–153
See application file for complete search history.

(56) References Cited

U.S. PATENT DOCUMENTS

| | | |
|---|---|---|
| 3,215,136 A | 11/1965 | Holter et al. |
| 4,123,785 A | 10/1978 | Cherry et al. |
| 4,532,934 A | 8/1985 | Kelen |
| 4,550,502 A | 11/1985 | Grayzel |
| 4,716,903 A | 1/1988 | Hansen |
| 4,809,705 A | 3/1989 | Ascher |

(Continued)

FOREIGN PATENT DOCUMENTS

| | | |
|---|---|---|
| DE | 19955211 | 5/2001 |
| WO | WO03/032192 | 4/2003 |

(Continued)

OTHER PUBLICATIONS

Chen et al. "Monitoring Body Temperature of Newborn Infants At Neonatal Intensive Care Units Using Wearable Sensors," BodyNets'2010, Corfu Island, Greece. (Sep. 10-12, 2010).

(Continued)

*Primary Examiner* — Linda Dvorak
*Assistant Examiner* — Brian M Antiskay
(74) *Attorney, Agent, or Firm* — Patterson Thuente Pedersen, P.A.

(57) ABSTRACT

An ambulatory electrocardiographic (ECG) monitor with a jumpered sensing electrode and method of use for female and large-girthed patients is provided. Self-powered ECG sensing circuitry is fully enclosed in a housing with electrode receptacles on a bottom surface. A flexible and stretchable electrode mounting panel is provided with a layer of skin adhesive. A standoff pad is placed between the housing and the electrode mounting panel. Sensing electrodes are mounted on opposite ends of the mounting panel. Each sensing electrode includes an electrode pad facing the skin contacting surface and an oppositely-facing electrode plug. Each plug is removably and pivotably couplable into the receptacles. A jumper wire assembly includes a jumper plug electrically connected to a jumper receptacle. The jumper plug is removably and pivotably couplable into the receptacles and the jumper receptacle is removably and pivotably couplable into the plugs on the mounting panel opposite from the standoff pad.

16 Claims, 12 Drawing Sheets

(56) References Cited

U.S. PATENT DOCUMENTS

| | | | |
|---|---|---|---|
| 4,915,656 A * | 4/1990 | Alferness | 439/729 |
| 5,168,876 A | 12/1992 | Quedens et al. | |
| 5,215,098 A | 6/1993 | Steinhaus | |
| D341,423 S | 11/1993 | Bible | |
| 5,392,784 A | 2/1995 | Gudaitis | |
| D357,069 S | 4/1995 | Plahn et al. | |
| 5,402,780 A * | 4/1995 | Faasse, Jr. | 600/392 |
| 5,402,884 A | 4/1995 | Gilman et al. | |
| 5,458,141 A | 10/1995 | Neil | |
| 5,473,537 A | 12/1995 | Glazer et al. | |
| 5,579,919 A | 12/1996 | Gilman et al. | |
| 5,582,181 A | 12/1996 | Ruess | |
| D377,983 S | 2/1997 | Sabri et al. | |
| 5,623,935 A | 4/1997 | Faisandier | |
| 5,697,955 A | 12/1997 | Stolte | |
| 5,749,902 A | 5/1998 | Olson et al. | |
| 5,817,151 A | 10/1998 | Olson et al. | |
| 5,850,920 A | 12/1998 | Gilman et al. | |
| D407,159 S | 3/1999 | Roberg | |
| 5,906,583 A | 5/1999 | Rogel | |
| 5,951,598 A | 9/1999 | Bishay et al. | |
| 5,984,102 A | 11/1999 | Tay | |
| 6,101,413 A | 8/2000 | Olson et al. | |
| 6,115,638 A | 9/2000 | Groenke | |
| 6,117,077 A | 9/2000 | Del Mar et al. | |
| 6,134,479 A | 10/2000 | Brewer et al. | |
| 6,148,233 A | 11/2000 | Owen et al. | |
| 6,269,267 B1 | 7/2001 | Bardy et al. | |
| 6,272,385 B1 | 8/2001 | Bishay et al. | |
| 6,301,502 B1 | 10/2001 | Owen et al. | |
| 6,304,773 B1 | 10/2001 | Taylor et al. | |
| 6,304,780 B1 | 10/2001 | Owen et al. | |
| 6,304,783 B1 | 10/2001 | Lyster et al. | |
| 6,374,138 B1 | 4/2002 | Owen et al. | |
| 6,418,342 B1 | 7/2002 | Owen et al. | |
| 6,427,083 B1 | 7/2002 | Owen et al. | |
| 6,456,872 B1 | 9/2002 | Faisandier | |
| 6,546,285 B1 | 4/2003 | Owen et al. | |
| 6,605,046 B1 | 8/2003 | Del Mar | |
| 6,607,485 B2 | 8/2003 | Bardy | |
| 6,671,545 B2 | 12/2003 | Fincke | |
| 6,671,547 B2 | 12/2003 | Lyster et al. | |
| 6,694,186 B2 | 2/2004 | Bardy | |
| 6,704,595 B2 | 3/2004 | Bardy | |
| 6,705,991 B2 | 3/2004 | Bardy | |
| 6,754,523 B2 | 6/2004 | Toole | |
| 6,782,293 B2 * | 8/2004 | Dupelle et al. | 607/142 |
| 6,860,897 B2 | 3/2005 | Bardy | |
| 6,866,629 B2 | 3/2005 | Bardy | |
| 6,887,201 B2 | 5/2005 | Bardy | |
| 6,893,397 B2 | 5/2005 | Bardy | |
| 6,904,312 B2 | 6/2005 | Bardy | |
| 6,908,431 B2 | 6/2005 | Bardy | |
| 6,913,577 B2 | 7/2005 | Bardy | |
| 6,944,498 B2 | 9/2005 | Owen et al. | |
| 6,960,167 B2 | 11/2005 | Bardy | |
| 6,978,169 B1 | 12/2005 | Guerra | |
| 6,993,377 B2 | 1/2006 | Flick et al. | |
| 7,020,508 B2 | 3/2006 | Stivoric et al. | |
| 7,027,864 B2 | 4/2006 | Snyder et al. | |
| 7,065,401 B2 | 6/2006 | Worden | |
| 7,085,601 B1 | 8/2006 | Bardy et al. | |
| 7,104,955 B2 | 9/2006 | Bardy | |
| 7,134,996 B2 | 11/2006 | Bardy | |
| 7,147,600 B2 | 12/2006 | Bardy | |
| 7,215,991 B2 | 5/2007 | Besson et al. | |
| 7,248,916 B2 | 7/2007 | Bardy | |
| 7,257,438 B2 | 8/2007 | Kinast | |
| D558,882 S | 1/2008 | Brady | |
| 7,328,061 B2 | 2/2008 | Rowlandson et al. | |
| 7,412,395 B2 | 8/2008 | Rowlandson et al. | |
| D606,656 S | 12/2009 | Kobayashi et al. | |
| 7,756,721 B1 | 7/2010 | Falchuk et al. | |
| 7,787,943 B2 | 8/2010 | McDonough | |
| 7,874,993 B2 | 1/2011 | Bardy | |
| 7,881,785 B2 | 2/2011 | Nassif et al. | |
| D639,437 S | 6/2011 | Bishay et al. | |
| 7,959,574 B2 | 6/2011 | Bardy | |
| 8,231,539 B2 | 7/2012 | Bardy | |
| 8,231,540 B2 | 7/2012 | Bardy | |
| 8,239,012 B2 | 8/2012 | Felix et al. | |
| 8,260,414 B2 | 9/2012 | Nassif et al. | |
| 8,266,008 B1 | 9/2012 | Siegel et al. | |
| 8,277,378 B2 | 10/2012 | Bardy | |
| 8,285,370 B2 | 10/2012 | Felix et al. | |
| 8,308,650 B2 | 11/2012 | Bardy | |
| 8,366,629 B2 | 2/2013 | Bardy | |
| 2002/0120310 A1 | 8/2002 | Linden et al. | |
| 2002/0193668 A1 | 12/2002 | Munneke | |
| 2003/0004547 A1 | 1/2003 | Owen et al. | |
| 2003/0073916 A1 | 4/2003 | Yonce | |
| 2003/0083559 A1 | 5/2003 | Thompson | |
| 2003/0139785 A1 | 7/2003 | Riff et al. | |
| 2004/0008123 A1 | 1/2004 | Carrender et al. | |
| 2004/0019288 A1 | 1/2004 | Kinast | |
| 2004/0034284 A1 | 2/2004 | Aversano et al. | |
| 2004/0049132 A1 | 3/2004 | Barron et al. | |
| 2004/0087836 A1 | 5/2004 | Green et al. | |
| 2004/0148194 A1 | 7/2004 | Wellons et al. | |
| 2004/0243435 A1 | 12/2004 | Williams | |
| 2004/0256453 A1 | 12/2004 | Lammle | |
| 2004/0260188 A1 | 12/2004 | Syed et al. | |
| 2005/0096717 A1 | 5/2005 | Bishay et al. | |
| 2005/0108055 A1 | 5/2005 | Ott et al. | |
| 2005/0154267 A1 | 7/2005 | Bardy | |
| 2005/0182308 A1 | 8/2005 | Bardy | |
| 2005/0182309 A1 | 8/2005 | Bardy | |
| 2005/0228243 A1 | 10/2005 | Bardy | |
| 2005/0245839 A1 | 11/2005 | Stivoric et al. | |
| 2006/0025824 A1 | 2/2006 | Freeman et al. | |
| 2006/0041201 A1 | 2/2006 | Behbehani et al. | |
| 2006/0122469 A1 | 6/2006 | Martel | |
| 2006/0224072 A1 | 10/2006 | Shennib | |
| 2006/0235320 A1 | 10/2006 | Tan et al. | |
| 2006/0253006 A1 | 11/2006 | Bardy | |
| 2007/0003115 A1 | 1/2007 | Patton et al. | |
| 2007/0050209 A1 | 3/2007 | Yered | |
| 2007/0078324 A1 | 4/2007 | Wijisiriwardana | |
| 2007/0093719 A1 | 4/2007 | Nichols, Jr. et al. | |
| 2007/0100667 A1 | 5/2007 | Bardy | |
| 2007/0123801 A1 | 5/2007 | Goldberger et al. | |
| 2007/0136091 A1 | 6/2007 | McTaggart | |
| 2007/0179357 A1 | 8/2007 | Bardy | |
| 2007/0203415 A1 | 8/2007 | Bardy | |
| 2007/0203423 A1 | 8/2007 | Bardy | |
| 2007/0225611 A1 | 9/2007 | Kumar et al. | |
| 2007/0244405 A1 | 10/2007 | Xue et al. | |
| 2007/0249946 A1 | 10/2007 | Kumar et al. | |
| 2007/0255153 A1 | 11/2007 | Kumar et al. | |
| 2007/0265510 A1 | 11/2007 | Bardy | |
| 2007/0276270 A1 | 11/2007 | Tran | |
| 2007/0293738 A1 | 12/2007 | Bardy | |
| 2007/0293739 A1 | 12/2007 | Bardy | |
| 2007/0293740 A1 | 12/2007 | Bardy | |
| 2007/0293741 A1 | 12/2007 | Bardy | |
| 2007/0293772 A1 | 12/2007 | Bardy | |
| 2008/0051668 A1 | 2/2008 | Bardy | |
| 2008/0058661 A1 | 3/2008 | Bardy | |
| 2008/0139953 A1 | 6/2008 | Baker et al. | |
| 2008/0194927 A1 | 8/2008 | KenKnight et al. | |
| 2008/0208014 A1 | 8/2008 | KenKnight et al. | |
| 2008/0284599 A1 | 11/2008 | Zdeblick et al. | |
| 2008/0288026 A1 | 11/2008 | Cross et al. | |
| 2008/0306359 A1 | 12/2008 | Zdeblick et al. | |
| 2009/0069867 A1 | 3/2009 | KenKnight et al. | |
| 2009/0216132 A1 | 8/2009 | Orbach | |
| 2009/0270747 A1 | 10/2009 | Van Dam et al. | |
| 2009/0292194 A1 | 11/2009 | Libbus et al. | |
| 2010/0022897 A1 | 1/2010 | Parker et al. | |
| 2010/0081913 A1 | 4/2010 | Cross et al. | |
| 2010/0185063 A1 | 7/2010 | Bardy | |
| 2010/0191154 A1 | 7/2010 | Berger et al. | |
| 2012/0088998 A1 | 4/2012 | Bardy et al. | |
| 2012/0089000 A1 | 4/2012 | Bishay et al. | |

(56) References Cited

U.S. PATENT DOCUMENTS

| | | |
|---|---|---|
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0101396 A1 | 4/2012 | Solosko et al. |
| 2012/0302906 A1 | 11/2012 | Felix et al. |
| 2013/0123651 A1 | 5/2013 | Bardy |
| 2013/0158361 A1 | 6/2013 | Bardy |

FOREIGN PATENT DOCUMENTS

| | | |
|---|---|---|
| WO | WO2006/014806 | 2/2006 |
| WO | 2007092543 | 8/2007 |
| WO | 2008010216 | 1/2008 |
| WO | WO2009/112976 A1 | 9/2009 |
| WO | WO2009/112978 A1 | 9/2009 |
| WO | WO2009/112979 A1 | 9/2009 |
| WO | WO2010/066507 | 6/2010 |

OTHER PUBLICATIONS

Lauren Gravitz, "When Your Diet Needs a Band-Aid," Technology Review, MIT. (May 1, 2009).

15 of the Hottest Wearable Gadgets—http://thehottestgadgets.com/2008/09/the-15-hottest-wearable-gadgets-001253.

P. Libby et al., "Braunwald's Heart Disease—A Textbook of Cardiovascular Medicine," Chs. 11, pp. 125-148 and 12, pp. 149-193 (8th ed. 2008), American Heart Association.

Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.

Epstein, Andrew E. et al.; ACC/AHA/HRS 2008 Guidelines for Device-Based Therapy of Cardiac Rhythm Abnormalities. J. Am. Coll. Cardiol. 2008; 51; e1-e62, 66 Pgs.

Kligfield, Paul et al., Recommendations for the Standardization and Interpretation of the Electrocardiogram: Part I. J.Am. Coll. Cardiol; 2007; 49; 1109-27, 75 Pgs.

Lieberman, Jonathan, "How Telemedicine Is Aiding Prompt ECG Diagnosis In Primary Care," British Journal of Community Nursing, vol. 13, No. 3, Mar. 1, 2008, pp. 123-126, XP009155082, ISSN: 1462-4753.

EPO Extended Search Report for Application No. 11184156.5-2319/2438848 Dated Apr. 27, 2012, 10 Pgs.

EPO Extended Search Report for Application No. 11184382.7-2201 Dated Jan. 23, 2012, 11 Pgs.

EPO Extended Search Report for Application No. 11184379.3-1225 Dated Jan. 26, 2012, 6 Pgs.

EPO Extended Search Report for Application No. 11184344.7-1265/2438852 Dated Jun. 6, 2012, 6 Pgs.

EPO Extended Search Report for Application No. 11184341.3-1265/2438851 Dated Jun. 8, 2012, 6 Pgs.

EPO Extended Search Report for Application No. 11184353.8-1265/2438854 dated Jul. 11, 2012, 10 pages.

EPO Extended Search Report for Application No. 11184347.0-1265/2438853 dated Jul. 11, 2012, 11 pages.

US 6,527,714, 03/2003, Bardy (withdrawn)

\* cited by examiner

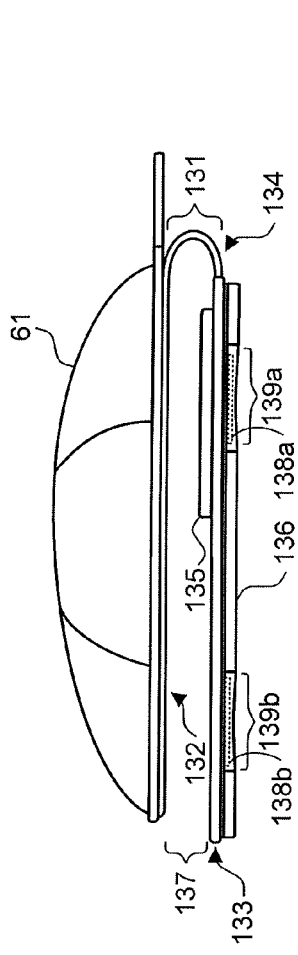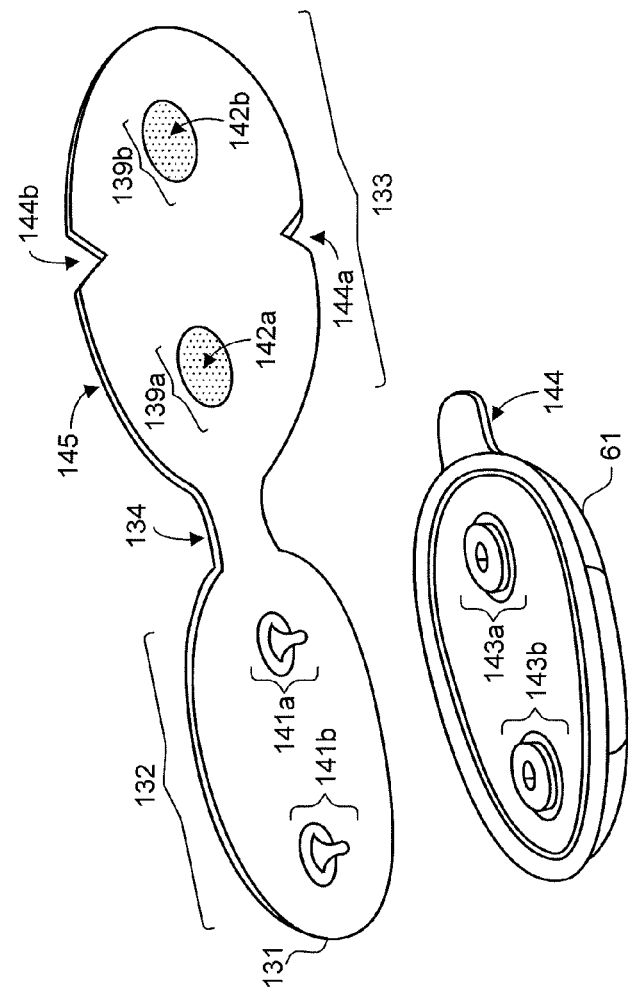
Fig. 13.
130
Fig. 14.
140

150

160

170

180

190

200

210

220

AMBULATORY ELECTROCARDIOGRAPHIC MONITOR FOR PROVIDING EASE OF USE IN WOMEN

CROSS-REFERENCE TO RELATED APPLICATION

This patent application is a continuation-in-part application of U.S. patent application, Ser. No. 12/901,428, filed Oct. 8, 2010 now abandoned, the priority date of which is claimed and the disclosure of which is incorporated by reference.

FIELD

This application relates in general to ambulatory electrocardiography and, in particular, to an ambulatory electrocardiographic monitor with jumpered sensing electrode for providing ease of use in women and method of use.

BACKGROUND

The cardiac electrical signal begins in the cells of the sinoatrial node in the right atrium. These cells spontaneously depolarize and create a cardiac action potential of electrical impulses that rapidly propagates outward across the right atrium and then the left atrium. The cardiac action potential in turn stimulates muscle cells of the atrial myocardium to depolarize and contract to push blood into the ventricles. Shortly thereafter, this atrial action potential encounters the atrioventricular node located at the juncture of the atria and ventricles near the center of the heart. The atrioventricular node slightly delays cardiac action potential propagation into the ventricles to ensure complete drainage of blood from the atria. Thereafter, the muscle cells of the ventricular myocardium are activated by the electrical wave front and are stimulated into systolic contraction. After a rest and reset period, the complete the heart beat cycle repeats. Any disruption in this process, which can include heart block, sinus bradycardia, atrial fibrillation, and ventricular tachycardia, can lead to the symptoms ranging from dizziness to a sensation of heart fluttering or palpitations, loss of consciousness or even death. Being able to record the electrical signal of the heart is a fundamental diagnostic tool of every physician.

Identifying abnormal rhythms depends upon the manner in which and the amplitude of the depolarization signal of the muscle cells of the atrial and ventricular myocardium that in turn act as sequential voltage sources, which generate a current flow across the thoracic region of the body and result in a characteristic signal on the body surface. In a typical electrocardiographic (ECG) monitor, cardiac action potentials occur between 0.05 Hz to 150 Hz with a signal strength of around 3 mVp-p (peak-to-peak). Although miniscule, the current flow can be measured to characterize the electrical activity of the heart using an ECG monitor or similar device. Voltage differentials from pairings of the electrodes are filtered, amplified, and combined into P, QRS, and T complexes.

Conventionally, cardiac action potentials are detected through electrodes attached to the skin on the chest and limbs based on the American Heart Association's classic 12-lead placement model, such as P. Libby et al., "Braunwald's Heart Disease—A Textbook of Cardiovascular Medicine," Chs. 11 and 12 ($8^{th}$ ed. 2008), the disclosure of which is incorporated by reference. Both traditional in-clinic and ambulatory Holter-style ECG monitors follow the standard 12-lead model with variations on numbers and placement of leads. Generally, limb lead electrodes are placed on each arm and on the left leg, while precordial lead electrodes are placed on the left upper chest region over the heart in close proximity to the heart and at a location of strongest cardiac action potential signal strength. In turn, the monitoring circuitry relies on the superior signal strength from over-the-heart electrode placement and the relatively long signal vector length that is afforded by lead placement over a wider physical expanse of the body. For instance, based upon the large inter-electrode distances, signal amplification assumes a signal strength of around 3 mVp-p (peak-to-peak). The limb leads can be repositioned as necessary to compensate for variability in patient anatomy due to tissue and bone density and heart position.

The 12-lead placement model, however, is poorly suited to long-term ambulatory monitoring both from the perspective of comfort and from the perspective of reliability, particularly in adult women, as well as on other patients with large-girthed, fatty, or well-developed upper chest regions. The latter concern simply relates to how standard monitoring electrodes fall off with modest movement, as well as how signal quality diminishes when electrodes are placed over breast tissue, as is unavoidable in some women. In-clinic ECG monitoring, for instance, assumes that the patient will remain relatively stationary and that the limb leads can be repositioned as necessary to provide sufficient electrode separation for recording a signal of reasonable amplitude and to compensate for variability in patient anatomy. In contrast, during ambulatory monitoring, a woman's body is in continual motion, even during sleep, albeit to a lesser degree. Electrodes are apt to detach and signal quality degrades or is absent altogether.

Moreover, the strictly in-clinic nature of conventional 12-lead monitoring inherently compensates for differences in physical body size, as electrodes can be placed in their ordinary positions with electrical lead cables adjusting to anatomical differences. In ambulatory monitoring, however, physical characteristics of the human body play a major role in electrode adhesion and signal capture, both of which have a direct impact on long-term monitoring quality and efficacy. Physical characteristics vary significantly from patient to patient, and even for the same patient over time. For instance, bone structure, musculature, and fat tissue in the thoracic region all affect the aggregate density of body mass due to physiological differences in body type, gender, age, physical constitution, and posture. As well, bone density and musculature tends to drastically decrease in geriatric patients as a result of the natural ageing process. Increased body mass density increases signal impedance and noise. An ambulatory ECG monitor with electrode leads integrated into a unitary device would be impracticable, as one package size would not fit all patients, whereas using wired leads connected to a separate control unit increases patient discomfort, while adding complexity and decreasing reliability.

Additionally, in women, changes in body position, for instance, lying down, stretching, or bending over, can displace the positioning of the breasts and the corresponding changes in tissue and bone density can deleteriously affect any electrodes placed thereon. Breasts also exhibit pendulous motion in proportion to overall size in response to motor activities, such as walking, running, biking, or exercise. Such recurrent motion can act to progressively detach items adhered to the soft tissues, like the breasts, and are likely to irritate the skin when motion leads to electrode patch tension. Moreover, breast tissue can increases the distance between sensing electrodes placed and the underlying heart. Breast tissue may also force placement of the electrode in a suboptimal location for recording the cardiac signal to remain comfortable, especially during long-term monitoring. The tradeoff in women, especially active or large breasted, buxom women, can account for poor ECG signal quality.

Notwithstanding, Holter and other forms of ambulatory ECG monitors generally still rely on electrodes placed close to the heart as suggested by the 12-lead placement model. For instance, U.S. Pat. No. 3,215,136 issued Nov. 2, 1965 to Holter et al. discloses an electrocardiographic recording and playback means. Episodes of ventricular tachycardia, asystolic intervals, and ectopic heart activities are sensed by electrodes disposed on the patient's skin in a suitable location, with sufficient inter-electrode separation. These signals are ordinarily recorded via a compact recorder worn by the patient that records an electrocardiogram (ECG) while he engages in activities of daily living, which subsequently allows a cardiac specialist to temporally correlate patient symptoms and cardiac abnormalities with activities. A cardiac rhythm disorder, as well as the absence of a rhythm disorder during symptoms, can sometimes be identified by having the patient record those symptoms during the use of the Holter monitor.

U.S. Pat. No. 6,117,077 issued Sep. 12, 2000 to Del Mar et al. discloses a long-term ambulatory physiological recorder provided in a relatively planar and triangular-shaped recorder housing with three adhesive electrode pads. The recorder is fully self-contained and mounted immediately adjacent to the organ system that is to be monitored. Electrode pads are adhesively and conductively attached to the patient's left chest in a position generally over the heart with positive and negative terminals in a relative vertical position from the top to the bottom of the heart. Additional electrode leads can also be connected to an input port on the recorder and placed over adjacent areas of the upper chest.

U.S. Pat. No. 6,456,872 issued Sep. 24, 2002 to Faisandier discloses a Holter-type apparatus for recording physiological signals indicative of cardiac activity. A base unit is formed of a flexible sheet carrying electrodes and a recording case that carries a battery and flexible printed circuit material. The base unit is disposable and can be changed with each new patient examination. The recorder case is fixed in position on the patient's thorax through a plurality of electrodes affixed either through adhesion or through depression using suction cups. Alternatively, the base unit can be carried by a thoracic belt or a hanging strap collar. The recording case includes electronic circuits for the collection and processing of ECG signals and a data transmission port is provided for by-directional exchange of data, control parameters, and information.

U.S. Pat. No. 7,257,438 issued Aug. 14, 2007 to Kinast discloses a patient-worn medical monitoring device that includes a lanyard and electronics package supported in the manner of a pendant. A lanyard includes integral electrodes or other sensors for making physiological measurements, which may be stored in a monitor for later readout or transmitted, before or after processing, to a remote location. The device can locally process and analyze a patient's signals and transmit only summary data or analyzed results to a remote device.

Finally, U.S. Patent application, Publication No. 2007/0255153, filed Nov. 1, 2007, to Kumar et al.; U.S. Patent application, Publication No. 2007/0225611, filed Feb. 6, 2007, to Kumar et al.; and U.S. Patent application, Publication No. 2007/0249946, filed Feb. 6, 2007, to Kumar et al. disclose discloses a non-invasive cardiac monitor and methods of using continuously recorded cardiac data. A heart monitor suitable for use in primary care includes a self-contained and sealed housing. The housing encloses an electronic memory connected to electrodes on the upper left chest to detect an ECG. A thin, flexible, and tapered rim or lip is provided around the edges of the electronics portion of the monitor to increase the surface area available for adhesion. Continuously recorded cardiac monitoring is provided through a sequence of simple detect-store-offload operations that are performed by a state machine. The housing is adapted to remain affixed to a patient for at least seven days. The heart monitor can include an activation or event notation button, the actuation of which increases the fidelity of the ECG information stored in the memory. The stored information can be retrieved and analyzed offline to identify both normal and abnormal ECG events. The monitor is specifically intended to provide monitoring continuously and without interruption over an extended period. Despite the improvement in size and ease of use of such a system, neither this device or any of the above described systems defines a device capable of extremely simple and reliable application for any body habitus and by any individual regardless of training. The application of this monitor is especially problematic for large breasted, buxom women.

Finally, U.S. Patent application, Publication No. 2008/0284599, filed Apr. 28, 2006, to Zdeblick et al. and U.S. Patent application, Publication No. 2008/0306359, filed Dec. 11, 2008, to Zdeblick et al., disclose a pharma-informatics system for detecting the actual physical delivery of a pharmaceutical agent into a body. An integrated circuit is surrounded by pharmacologically active or inert materials to form a pill, which dissolve in the stomach through a combination of mechanical action and stomach fluids. As the pill dissolves, areas of the integrated circuit become exposed and power is supplied to the circuit, which begins to operate and transmit a signal that may indicate the type, A signal detection receiver can be positioned as an external device worn outside the body with one or more electrodes attached to the skin at different locations. The receiver can include the capability to provide both pharmaceutical ingestion reporting and psychological sensing in a form that can be transmitted to a remote location, such as a clinician or central monitoring agency.

Therefore, a need remains for an ambulatory ECG monitoring device and method of use adapted to long term monitoring that resists body movement while providing ease and discreteness of use and patient comfort regardless of patient knowledge and regardless of patient body habitus. Additionally, such an ambulatory ECG monitoring device and method of use would preferably adapt to a wide range of different body characteristics and physiques, particularly ample-breasted women and other individuals with significant breast tissue.

SUMMARY

A small and anatomically adaptive ambulatory electrocardiogram monitor includes a disposable ECG monitor that is applied in-clinic by a primary care provider, by the patient at home, or by other healthcare or lay individuals to record ECG data over an extended time period while the patient engages in activities of daily living. The shape of the ECG monitor is adapted to placement on women and large-chested individuals. The patient's upper thoracic region is evaluated, including determining what affect breast physiology will have on extended placement of the ECG monitor. The ECG monitor is placed on the patient's chest at midline in the upper portion of the intermammary cleft, covering the center third of the sternum and centered between the manubrium and the xiphoid process on the inferior border of the sternum. This unique location for ECG monitor application and the monitor's small size allow for a uniformity of applicability by minimally trained physicians or even lay individuals. Upon completion of monitoring, the patient delivers the disposable monitor to a reading service, along with encoded patient medical information and a diary recording the patient's subjective impressions contemporaneous to the monitoring, such as described in commonly-assigned U.S. Patent application, entitled "Computer-Implemented System And Method For Evaluating Ambulatory Electrocardiographic Monitoring of Cardiac Rhythm Disorders," Ser. No. 12/901,461, filed Oct. 8, 2010, pending, the disclosure of which is incorporated by reference. A unique identifier assigned to the disposable monitor is also provided with the sealable envelope. The reading service interprets the ECG data and patient medical information and, where indications of a cardiac rhythm disorder or other health concern arise, an automated referral to a cardiac specialist, or other healthcare specialist, is made. The patient and his primary care provider are also informed.

One embodiment provides an ambulatory electrocardiographic (ECG) monitor with a jumpered sensing electrode and method of use for female and large-girthed patients. Self-powered ECG sensing circuitry is fully enclosed in a housing that provides electrode connection receptacles on a bottom surface of the housing. A flexible and stretchable electrode mounting panel having an elongated shape is provided with a layer of skin adhesive on a skin contacting surface. A standoff pad sized smaller than the electrode mounting panel is provided and defines an opening. The standoff pad is placed between the bottom surface of the housing and the electrode mounting panel with one of the electrode connection receptacles positioned within the opening. Sensing electrodes are mounted on opposite ends of the mounting panel. Each sensing electrode includes an electrode pad facing the skin contacting surface and an oppositely-facing electrode connection plug. Each connection plug is removably and pivotably couplable into the connection receptacles. A jumper wire assembly includes a jumper connection plug electrically connected to a jumper connection receptacle. The jumper connection plug is removably and pivotably couplable into the connection receptacles and the jumper connection receptacle is removably and pivotably couplable into the connection plugs on the mounting panel opposite from the standoff pad.

A further embodiment provides an ambulatory electrocardiographic (ECG) monitor with hinged sensing electrode mounting panel and method of use for female and large-girthed patients. Self-powered ECG sensing circuitry is fully enclosed in a housing that provides a pair of electrode connection receptacles on a bottom surface of the housing. A flexible and stretchable electrode mounting panel includes an upper panel facing the bottom surface of the housing and a lower panel hingably folded under the upper panel and having an elongated shape. A layer of skin adhesive on a skin contacting surface is provided. The standoff pad is placed over one of the sensing electrodes with the electrode connection plug positioned within the opening, and the upper panel and lower panel are hinged proximally to the standoff pad. A pair of sensing electrodes is mounted on opposite ends of the lower panel and includes an electrode pad facing the skin contacting surface. A pair of electrode connection plugs is removably and pivotably couplable into the electrode connection receptacles on the housing. Each connection plug is electrically connected to one of the sensing electrodes.

A still further embodiment provides an ambulatory electrocardiographic (ECG) monitor with extendable sensing electrode mounting panel and method of use for female and large-girthed patients. Self-powered ECG sensing circuitry is fully enclosed in a housing that provides a pair of electrode connection receptacles on a bottom surface of the housing. A flexible and stretchable electrode mounting panel having an elongated shape includes an extension panel collapsibly provided on one side of the electrode mounting panel. A layer of skin adhesive on a skin contacting surface of each of the electrode mounting panel and the extension panel is provided. The skin adhesive layer is independently suspended from the housing with a set of standoffs having non-uniform heights affixed to and defining an increasingly wide gap between the skin adhesive layer and a bottom surface of the housing. A pair of sensing electrodes is also provided, with one sensing electrode mounted on the extension panel and the other sensing electrode mounted on the electrode mounting panel distally from the extension panel-mounted sensing electrode. Each sensing electrode includes an electrode pad facing the skin contacting surface and an oppositely-facing electrode connection plug. The electrode connection plugs are removably and pivotably couplable into the electrode connection receptacles on the housing.

A still further embodiment provides An ambulatory electrocardiographic (ECG) monitor with an incrementally disposable sensing electrode mounting panel and method of use for female and large-girthed patients. Self-powered ECG sensing circuitry is fully enclosed in a housing that provides a pair of electrode connection receptacles on a bottom surface of the housing. A flexible and stretchable electrode mounting panel having an elongated shape includes a plurality of peel-away layers, which each include skin adhesive and a backing on an oppositely-facing surface. The peel-away layers are successively stacked with backing to skin adhesive. The outermost peel-away layer exposes the skin adhesive on a skin contacting surface of the electrode mounting panel. The peel-away layers are independently suspended from the housing with a set of standoffs having non-uniform heights affixed to and defining an increasingly wide gap between the skin adhesive layer and a bottom surface of the housing. A pair of sensing electrodes is mounted on the electrode mounting panel. Each sensing electrode includes an electrode pad facing the skin contacting surface and an oppositely-facing electrode connection plug. The electrode connection plugs are removably and pivotably couplable into the electrode connection receptacles on the housing.

An ambulatory ECG monitor in accordance with foregoing embodiments can be built at low cost, size and weight with a bill of materials of about one fifth of the cost of a conventional ambulatory ECG monitor. Low cost ambulatory monitors for other kinds of physiological monitoring, such as oxygenation and spirometry, could similarly be built, thereby facilitating a modular approach to long-term monitoring. As well, low cost enables clinics and hospitals to maintain ample inventory at all times to accommodate the ebb and flow of patients in need of ambulatory ECG monitoring. In turn, these patients will not need to wait on monitor availability or laboratory staffing for use and subsequent over read.

Additionally a single-use ECG monitor in the form of an adhesive patch in accordance with foregoing embodiments can be constructed with a weight of less than two ounces and inter-electrode spacing ranging from less than 6 cm to more than 9 cm, depending upon patient physique, which presents three advantages. First, costs for shipping the monitors to clinics, hospitals, pharmacies, and other locations are reduced, especially when large quantities must be mailed around the world. Second, small size and weight ambulatory ECG monitors can be easily carried in the pockets of health care providers and therefore applied upon demand without the need to either retrieve the monitors from a special location or to send the patient to a separate laboratory. Third, small, lightweight ambulatory ECG monitors, particularly with a jumpered sensing electrode, hinged sensing electrode mounting panel, extendable electrode mounting panel, or incrementally disposable sensing electrode mounting panel, reduce shear forces on the skin and overall usability, which further ensures good signal acquisition and long-term ECG recording by facilitating adherence to the skin and comfort for the patient.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 13 is a functional block diagram showing an ambulatory electrocardiographic monitor with hinged sensing electrode mounting panel in accordance with a further embodiment.

FIG. 14 is a functional block diagram showing the electrode mounting panel and the underside of the housing of the ambulatory electrocardiographic monitor of FIG. 13.

DETAILED DESCRIPTION

Figure 1:
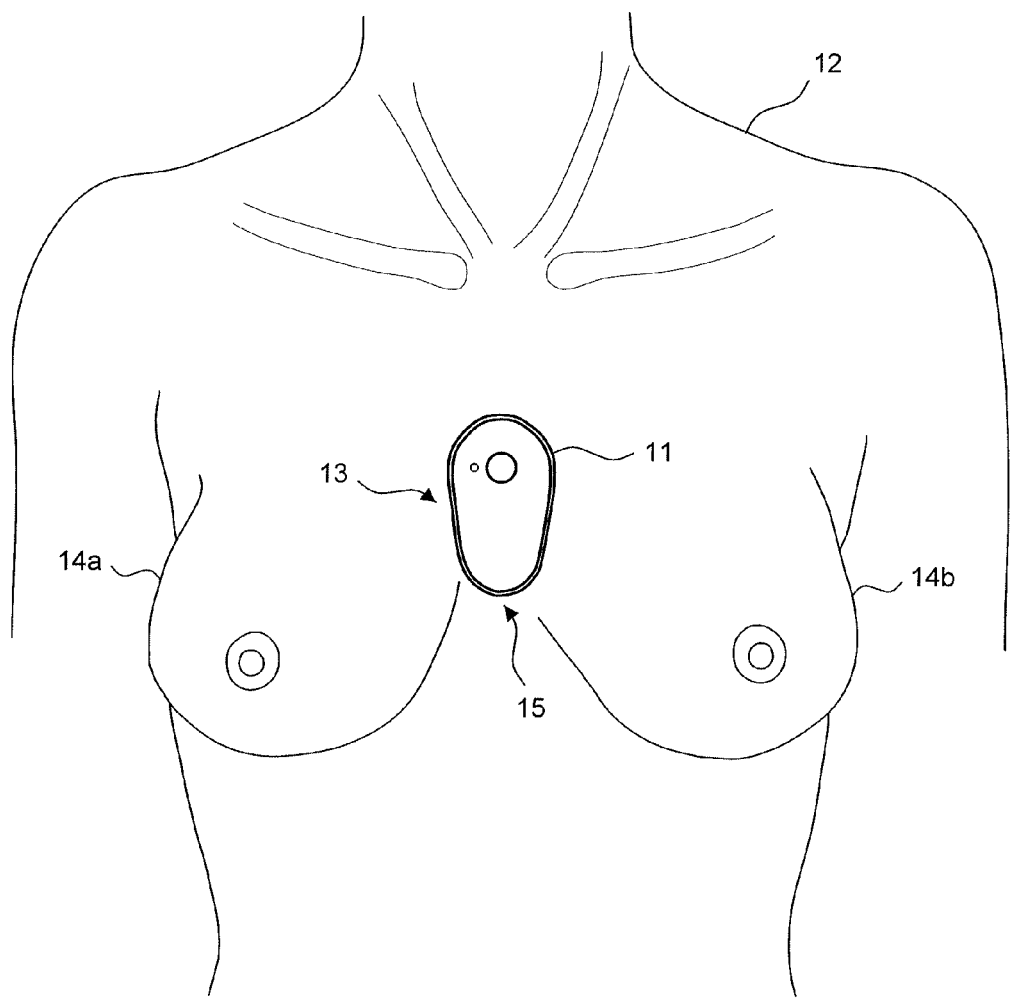
FIG. 1 is a front anatomical diagram showing placement of an ambulatory electrocardiographic monitor on a female patient.

Ambulatory ECG monitoring can be improved by locating the lead electrodes to body positions better adapted to minimize artifacts due to body movement. FIG. 1 is a front anatomical diagram 10 showing placement of an ambulatory electrocardiographic (ECG) monitor 11 on an adult female patient 12. Placement of the monitor 11 on an adult female patient 12 can require additional considerations to ensure safety, comfort, and long-term adhesion over the course of the monitoring period. The same considerations may apply on all patients with large-girthed, fatty, or well-developed breasts or chest areas, regardless of age and gender, to whom the present discussion is primarily focused. Placement of the monitor 11 on an adult male patient or patients with modest frames or chest areas is described in commonly-assigned U.S. Patent application, entitled "Ambulatory Electrocardiographic Monitor with Jumpered Sensing Electrode and Method of Use," Ser. No. 13/191,403, filed Jul. 26, 2011, pending, the disclosure of which is incorporated by reference. Notwithstanding, the monitor 11 can be used with a jumpered sensing electrode, a hinged sensing electrode mounting panel, or an extendable electrode mounting panel to accommodate a wide range of different body characteristics and physiques, such as respectively described below beginning with respect to FIGS. 8, 13, and 16. For clarity, the term "female" will apply to individuals in this entire class of patients without regard to age or gender or other physical characteristics or traits not germane to the selection of the monitoring site and placement of a monitor 11 on the patient's chest.

For these kinds of patients, the monitor 11 is placed between the breasts 14a, 14b in the upper portion of the intermammary cleft 15. The breast size, shape, position, symmetry, overall body physique, posture, and other factors, such as the type of brassiere worn and its fit or the presence of artificial implants are carefully evaluated relative to the size of the monitor 11 for ensuring that the monitor 11 does not overlap with, sit or press upon, and otherwise significantly interfere with the natural movement and positioning of the breasts 14a, 14b. The placement of the monitor 11 depends upon the width, length, depth, and relative location of the intermammary cleft 15. A skin adhesion layer of the monitor 11 is firmly adhered within the upper intermammary cleft 15 with the assembly housing the ECG recording circuitry bending in conformity to the shape of the sternum and being independently suspended above the skin adhesion layer to resist torsional body movement, as further described infra.

The monitor 11 may be applied in-clinic by a primary care provider, or by the patient herself, for instance, under a physician's orders after first obtaining the monitor 11 from a pharmacy or other authorized dispensary, such as described in commonly-assigned U.S. Patent application, entitled "Computer-Implemented System and Method for Mediating Patient-Initiated Physiological Monitoring," Ser. No. 12/901, 455, filed Oct. 8, 2010, pending, the disclosure of which is incorporated by reference. The monitor 11 is typically used over a 24-48 hour period, but the monitoring period could be extended from seven days up to 30 days through use of a series of monitors. During monitoring, the patient 12 engages in activities of daily living, while the monitor 11 unobtrusively monitors and collects ECG data. Recording commences upon physical application of the monitor 11 and ends when the monitor 11 is removed, typically by the patient 12. Along with the monitor 11, the patient 12 receives instructions for having the monitor 11 processed post-monitoring, which can be performed by a reading service, such as described in commonly-assigned U.S. Patent application, entitled "Computer-Implemented System And Method For Evaluating Ambulatory Electrocardiographic Monitoring of Cardiac Rhythm Disorders," cited supra. As appropriate, the patient 12 is referred to a medical specialist for follow up care, such as described in commonly-assigned U.S. Patent application, entitled "Computer-Implemented System and Method for Facilitating Patient Advocacy through Online Healthcare Provisioning," Ser. No. 12/901,433, filed Oct. 8, 2010, pending, the disclosure of which is incorporated by reference.

Figure 2:
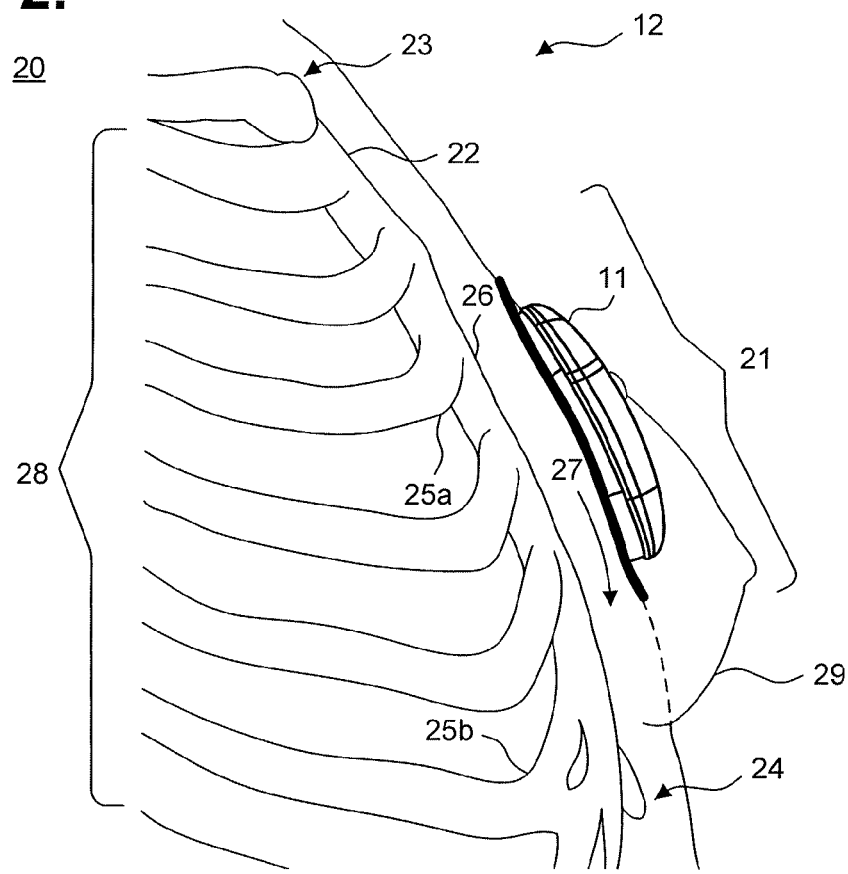
FIG. 2 is a cutaway anatomical diagram showing placement of the ambulatory electrocardiographic monitor of FIG. 1.

Proper placement of the monitor 11 is critical to recording high quality ECG data. FIG. 2 is a cutaway anatomical diagram 20 showing placement of the ambulatory electrocardiographic monitor 11 of FIG. 1. The ambulatory monitor 11 is removably adhered onto the skin on the patient's chest 21 at midline, covering the center third of the chest 21 over the sternum 26, roughly between the third and fifth ribs 25a-b and approximately centered between the suprasternal notch 23 on the superior border of the manubrium and the xiphoid process 24 on the inferior border of the sternum 26.

The midline sternum-centered monitoring site enables high P-wave and QRS-wave acquisition and provides several additional benefits over other more typical cutaneous monitoring locations like those locations over the left upper chest or in the left inframammary crease. First, electrical current originating from the atria and ventricles flow directly underneath the sternum 26 providing excellent P waves and QRS waves necessary for cardiac rhythm diagnosis. Signal quality is further improved by minimizing the depth of tissue, and noise thus generated by moving tissue, between the monitor's electrodes and the heart. Tissue depth is fairly consistent at the sternal midline where variations in the patient's weight and physical topology least interfere with ECG signal pickup. The midline sternum-centered location enables the monitor's electrodes to record an ECG of optimal signal quality from a location immediately above the strongest signal-generating aspects of the heart. Further, the surface of the skin located over the midline sternum-centered location remains relatively stationary, despite body motion or movement of underlying breast tissue 29, as well as muscle or other body tissue. Movement of the skin surfaces of the upper thoracic region can be of significant moment, particularly on obese patients or women with large or heavy breasts. Adhering the monitor 11 to a body position of minimal movement helps ensure that the monitor 11 remains adhered to the patient 12 throughout the entire monitoring period, as further described infra.

Figure 3:
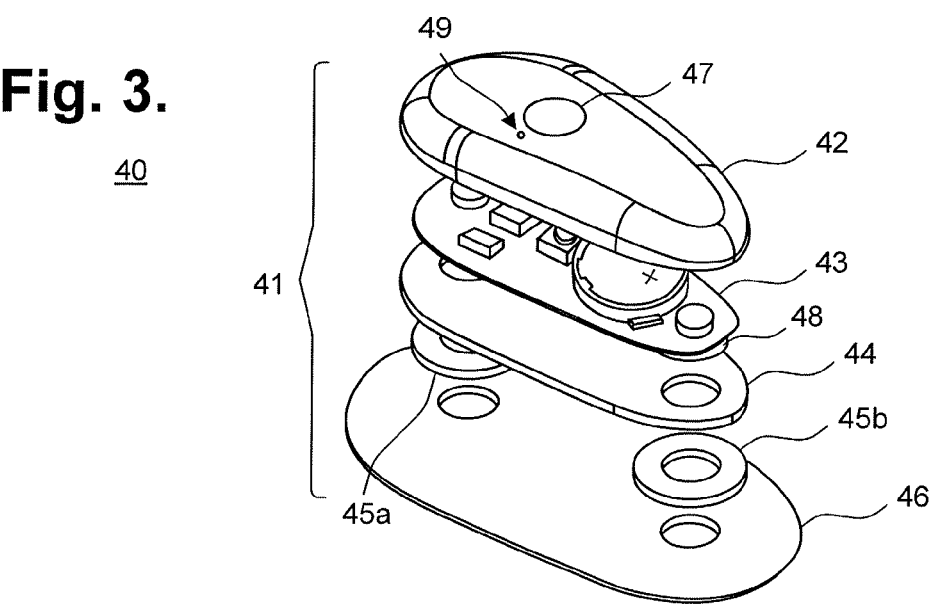
FIG. 3 is an exploded perspective view of an ambulatory electrocardiographic monitor in accordance with one embodiment.

The ambulatory ECG monitor is constructed to provide low cost widespread use, with a particular emphasis in improving patient care at the primary care medical practice level, especially for women. FIG. 3 is an exploded perspective view 40 of an ambulatory electrocardiographic monitor 41 in accordance with one embodiment. Physically, when viewed from above, the monitor 41 has an elongated triangular shape with rounded vertices, such as described in commonly-assigned U.S. Design Patent, entitled "Wearable Ambulatory Electrocardiographic Monitor," U.S. Pat. No. D639,437, issued Jun. 7, 2011, the disclosure of which is incorporated by reference, with dimensions of approximately 3.8 cm (1.5 in) wide and 7.6 cm (3.0 in) long with a pair of electrodes 48 spaced from less than 6 cm apart to more than 9 cm apart, depending upon patient physique. In addition, in a further embodiment, the spacing is adjustable by virtue of an extendable sensing electrode mounting panel, as further described below beginning with reference to FIG. 16. The monitor 41 weighs about 14.2 grams (0.5 oz) when assembled with electrodes 48 and a waterproof housing for the ECG recording circuitry, although a weight of up to 28 grams (1.0 oz) would be acceptable. In one embodiment, the pair of electrodes 48 have an approximately 5.33 cm spacing, although other electrode spacing, generally less than 6 cm, and combinations of three or more electrodes could also be used. When adhered onto a patient's sternum, the narrowest part of the monitor 41 faces downwards towards the patient's feet. On a female patient, the narrow part fits partway into the upper intermammary cleft 15. The small and narrow size, as well as the taper, allow the monitor 41 to fit comfortably between the breasts.

The monitor 41 is constructed in a modular fashion and includes a flexible housing and standoff-separated skin adhesion assembly. The housing includes a cover 42, printed circuit board (PCB) 43, and cover base 44, and the skin adhesion assembly includes a set of standoffs 45a-b, a layer of skin adhesive 46, and a set of electrodes 48. The housing protects the electronic components for sensing and recording ECG data, as further described below with reference to FIG. 7, which are affixed to the PCB 43. The cover 42 conformably fits against the edges of the cover base 44. The cover 42 and cover base 44 form a water resistant enclosure that fully enclose the PCB 43. In a further embodiment, the housing 61 is vented, which allows the cover 42 to slightly "give" when pressed. A button 47 is formed on the top surface of the cover 42 that engages a switch on the PCB 43, which the patient can press during monitoring to mark an event occurrence, such as onset of dyspnea. An indicator light 49, such as a light emitting diode, visually signals the patient 12 that the monitor 11 is working. A steady light signifies normal operation, while a blinking light indicates a problem.

The outer materials are selected for extended term use. The cover 42 and cover base 44 are both constructed from flexible bio-safe materials, such as plastic, silicon, or foam, and can be vacuum-formed, extruded, or die cut. The adhesive layer 46 is constructed using an adhesive fabric or cloth, which can be woven, as well as latex, foam, and other materials that sufficiently resist the twisting and torquing of the skin's surface. The skin adhesive could be, for instance, a single-coated silicon adhesive gel or elastomer film. In a further embodiment, darts are cut into the periphery of the adhesive layer 46 to more closely conform to an uneven or contoured skin surface, such as further described below with reference to FIGS. 10 and 14. Other materials and methods of manufacture are possible.

The housing and skin adhesion assembly facilitate long term monitoring. Continuous and uninterrupted wear of the monitor 41 over the entire course of monitoring may be impracticable for every patient. Skin sensitivities, allergies, irritation, and similar factors have an effect on a patient's ability to tolerate the wearing of the monitor 41 for an extended period. Similarly, oil on the skin's surface, perspiration, and overall physical hygiene can affect monitor adhesion. As a result, the housing can be separated from the skin adhesion assembly to allow the patient 12 to reposition or replace the skin adhesion assembly. The set of electrodes 48 fit within set of standoffs 45a-b and a set of holes 66a-b, or "gel wells," in the skin adhesive layer 46. In turn, the skin adhesive layer 46 is affixed to the cover base 44 through a combination of a pair of snap-on or similar form of removable connectors facing downwardly from the PCB 44 and adhesive applied to the upward facing surfaces of the standoffs 45a-b.

To facilitate overall long term monitoring through a series of short term monitoring periods, the housing can be separated from the skin adhesion layer and either a new skin adhesion layer can be applied, or the existing skin adhesion layer can be repositioned. In a still further embodiment, a stack of peel-away layers of disposable skin adhesive pads can be provided, such as further described below beginning with FIG. 21. Either the same housing or a new housing can be used during successive periods of monitoring. When the same housing is reused, the recording circuitry compensates for disconnection and reconnection of the sensing electrodes by stopping recording of ECG data during the gap in monitoring, as sensed by disconnection from the set of electrodes 48. The recording circuitry thereafter resumes recording upon being reconnected to a set of electrodes 48. If necessary, the patient 12 may choose to take a break and allow her skin to "breathe" between applications of the skin adhesion layer.

In one embodiment, the monitoring circuit for ECG recording used by the monitor 10 operates under microprogrammed control on a single channel of analog input signals. The signals originate as cardiac action potentials sensed from the skin's surface by a single sensing electrode pair, although multiple sensing electrode pairs could be employed with modifications to the monitoring circuit to factor in multiple input signal channels. The analog input signals are converted into digitized form and encoded for efficient compressed data storage in non-volatile memory. The monitoring circuit injects a reference feedback signal into both the analog input signal path and the patient's body. Thus, noise generated by the electronics is integrated into the input signals, rather than being filtered or rejected. The monitoring circuit is thereby able to operate unshielded, with no filtering, and through minimal power filtering components, which thereby eliminates the need for either the cover 42 or cover base 44 to include physical noise shielding is eliminated through unique printed circuit board design and layout, as well as careful selection of electronic components that naturally dampen received noise. As well, the digitization and compression of the original low noise analog signal requires less memory to store long term ECG data.

Referring back to FIG. 2, the body's surface over the sternum 26 is inherently uneven, even in children, due to the underlying bone structure of the body of the sternum 26 and ribs 28, as well as the muscle, fat, skin, and various tissue that cover the sternum 26 and adjacent regions. The front surface of the body of the sternum 26 is slightly convex in the east-west directions and the sternum's front surface angles in towards the thoracic cavity from around the fourth intercostal space 27 down to the xiphoid process 24 in the north-south directions. In the elderly, particularly in older males, the east-west convexity can become increasingly pronounced with age, resulting in a so-called "pigeon-chested" appearance.

Figure 4:
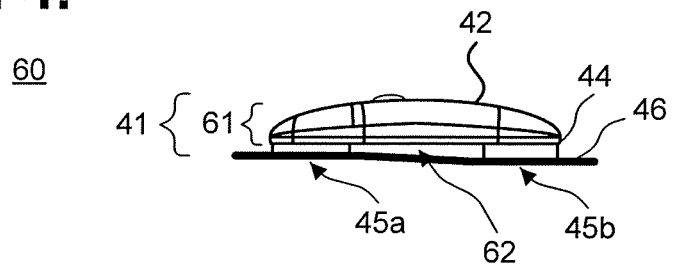
FIG. 4 is a side view of the ambulatory electrocardiographic monitor of FIG. 3.
Figure 5:
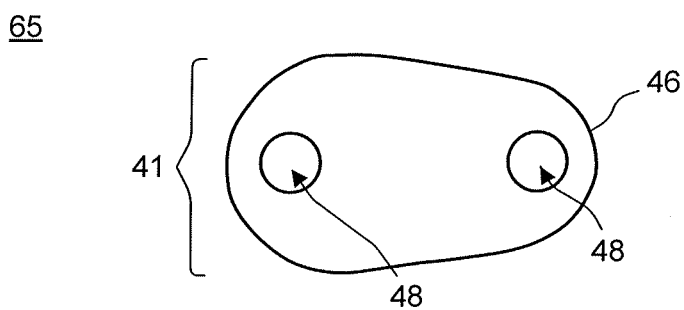
FIG. 5 is a bottom view of the ambulatory electrocardiographic monitor of FIG. 3.

Conforming fit and secure adhesion to this inherently uneven surface are provided through two interconnected structures: a flexible housing and standoff-separated skin adhesion assembly. FIGS. 4 and 5 are respectively side and bottom views 60, 65 of the ambulatory electrocardiographic monitor 41 of FIG. 3. The monitor 41 must adhere to the sternum 26 during the monitoring period. The cover 42 and cover base 44 provide a housing 61 for the monitor's electronic components. In one embodiment, the PCB 43 is about 0.02" thick, which allows the PCB 43 to conform to the east-west convexity of the sternum 26 and to the natural north-sound inward curve towards the xiphoid process 24.

Objects adhered to the sternum 26 need to be able to both conform statically to the shape of the chest 21 and to accommodate dynamic torsional movement, as occurs during stretching, sleeping, and other body movement. The PCB 43 can bend axially and laterally, but the PCB's ability to stretch is limited by physical constraints on electronics packaging. To provide stretch, the monitor 41 utilizes a form of independent suspension that enables the skin adhesive layer 46 to stretch, as well as flex, independently of the housing 61. The monitor 41 is adhered to the patient's skin through a layer of skin adhesive 46 that is affixed to the bottom surface of the cover base 44 around the set of standoffs 45a-b. The skin adhesive layer 46 is slightly larger than the bottom of the cover base 44 by about 0.125 in, although other shapes, sizes, and dimensions could be used, including shapes that differ significantly from the top profile of the cover base 44. The set of electrodes 48 are removably affixed to a pair of snap-on connectors facing downwardly from the PCB 44 and are electronically connected to the PCB's circuitry. Other types of connectors that allow the set of electrodes 48 to be removably affixed could also be used. The set of electrodes 48 fit within openings formed in the set of standoffs 45a-b and a set of holes 66a-b, or "gel wells," in the skin adhesive layer 46. The electrodes 48 are coated with a conductive gel that also assists with adhering the monitor 41 to the patient's chest 21. The independent suspension is provided through the set of two or more standoffs 46a-b that create a gap 62 of about 2.5 mm (0.1 in) to about 6.3 mm (0.25 in) between the bottom surface of the cover base 44 and the top surface of the skin adhesive layer 46. The heights of each of the standoffs 45a-b define an increasingly wide gap between the bottom of the housing 61 and the adhesive layer 46, which permits the monitor 41 to stay securely attached to the patient 12 during torsional movement, such as occurs when stretching or rolling over in bed. The standoffs 45a-b have non-uniform heights to compensate for the unevenness of the female anatomy, as further described below with reference to FIG. 6. The gap 62 allows the housing 61 to "float" above the skin contact surface, while the skin adhesive layer 46 can flex and stretch along with the skin's surface on the patient's sternum chest 21. The single-point contact of each of the standoffs 45a-b thus allows the monitor 41 to accommodate the patient's twisting and turning movements and remain affixed without danger of peeling off.

Figure 6:
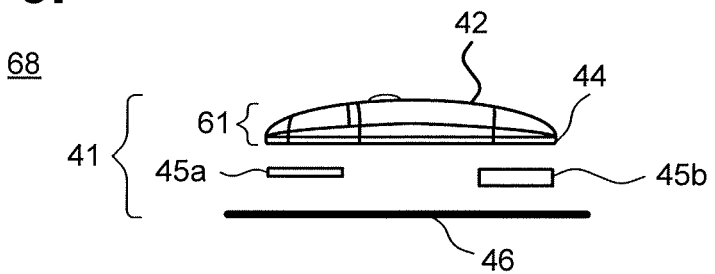
FIG. 6 is an exploded side view of the ambulatory electrocardiographic monitor of FIG. 3.

Breast tissue 29 (shown in FIG. 2) can increases the distance between sensing electrodes 48 placed and the underlying heart. FIG. 6 is an exploded side view 68 of the ambulatory electrocardiographic monitor 41 of FIG. 3. The degree of inward curvature of the sternum's front surface towards the thoracic cavity is more pronounced in women than in men. The PCB 43 permits north-south flex of housing 61, but the amount of inward flex may be insufficient to securely adhere the monitor 41 to an adult female's chest 21. To help compensate for the inward angle of the body of the sternum past the fourth intercostal space 27, especially in women, the standoffs 45b located on the narrowest part of the monitor 41 have slightly greater heights. In one embodiment, the shorter standoffs 45*a* have a height of about 2.5 mm (0.1 in) and the taller standoffs 45*b* have a height of about 6.3 mm (0.25 in).

Figure 7:
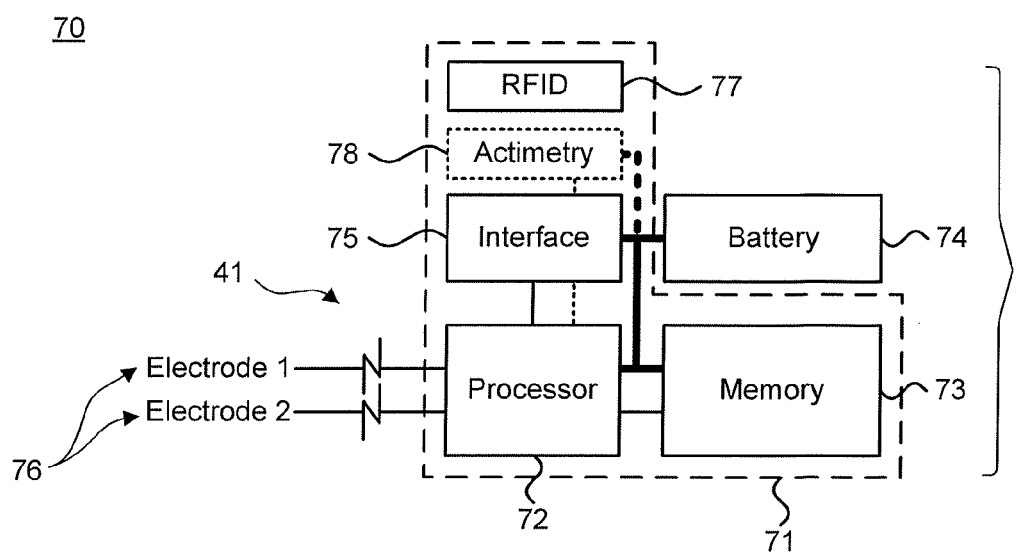
FIG. 7 is a functional block diagram showing the groups of electronic component of the ambulatory electrocardiographic monitor of FIG. 3.

The electronics package of each monitor facilitates low-cost extended wear use. FIG. 7 is a functional block diagram 70 showing the groups of electronic components 71 of the ambulatory electrocardiographic monitor 41 of FIG. 3. The monitor 41 is self-contained and operates under microprogrammed control, such as described in commonly-assigned U.S. Patent application, entitled "Microcontrolled Electrocardiographic Monitoring Circuit with Feedback Control," Ser. No. 12/901,449, filed Oct. 8, 2010, pending, and U.S. Patent application, entitled "Microcontrolled Electrocardiographic Monitoring Circuit with Differential Voltage Encoding," Ser. No. 12/901,460, filed Oct. 8, 2010, pending, the disclosures of which are incorporated by reference. Digitally-controlled ECG monitoring circuits provide the ability to handle the wide dynamic range occasioned by the short signal vector and low signal strength afforded by a midline sternum-centered ambulatory monitoring location.

In a functional sense, the electronic components 71 can be grouped into circuitry for a processor 72, memory 73, power supply or battery 74, data interface 75, and radio frequency identification (RFID) tag 77. The processor 72 is a discrete ECG recording circuit that operates under microprogrammed control on a single channel of analog input signals. To sense ECG data, the processor 72 interfaces to a set of external electrodes 76 through amplifiers and filters (not shown). Signals originate as action potentials sensed on the skin's surface by at least one of the electrodes 76 and a feedback signal is output through the other electrode 76. The sensed ECG data is processed into a stream of discrete digital values and encoded in the persistent non-volatile memory 73, which can be implemented as electrically-erasable programmable read-only memory (EEPROM) or "flash" memory. The data interface 75 enables the processor 71 to download recorded ECG data from the memory 73 and receive programming instructions. The processor 71, memory 72, and data interface 74 can be a single discrete integrated circuit or a set of individual components interconnected through data channels. The battery 74 is a conventional power cell or capacitor that provides power to the recording circuitry sufficient to enable extended operation.

In a further embodiment, either or both of the memory 73 and the battery 74 can be separately provided on the skin adhesion layer 46 to facilitate long term monitoring through use of a series of short term monitoring periods. Space for storing recorded ECG data and power for operating the recording circuitry are continually depleted. Providing the memory 73 and the battery 74 on the skin adhesion layer 46 enables those resources to be replenished, while enabling use of the same physical recording circuitry throughout the entire monitoring period.

The RFID tag 77 contains a unique identifier for the monitor that is either included on the PCB 43 with the other electronic components, or is embedded into the housing 61, such as within a foam-constructed cover 42. The RFID tag 77 is used during monitoring to pair a monitor 41 to a tracking number that can be used by the patient 12, referral center, and physician or staff to track the physical whereabouts of the monitor 41 and to determine the post-monitoring status of diagnosis and follow up care. The RFID tag 77 is self-powered or can be powered through the battery 74. The RFID tag 77 is accessed using standard RFID transmitter and receiver units. Other components in addition to or in lieu of the electronic components 71 are possible, such as used to record additional types of patient physiometry or to provide further onboard capabilities.

In a further embodiment, the electronic components 71 also include an actimetry sensor 78 to measure gross motor activity undertaken by the patient, such as through walking, running, changing posture or sleep position, and other body motions. For instance, the actimetry sensor 78 may record movement, which indicates that the patient was climbing stairs at the same time that an increase in heart rate was recorded by the monitor 11. Particularly, when actigraphy is combined with the patient's subjective impressions as contemporaneously recorded in his diary, the physician can confirm or better understand hemodynamic changes and other aspects of cardiac physiology as reflected in the recorded ECG data.

The monitor 41 may be fully or partially disposable. For instance, the electronic components 71 on the PCB 43 may be refurbished and recycled for multiple uses, while the housing 61 and skin adhesive 46 would be disposed after a single use. During refurbishment, the battery 74 would be replaced and the memory 73 wiped clean. Alternatively, the entire monitor 41 may be used only once, followed by appropriate disposal.

Figure 8:
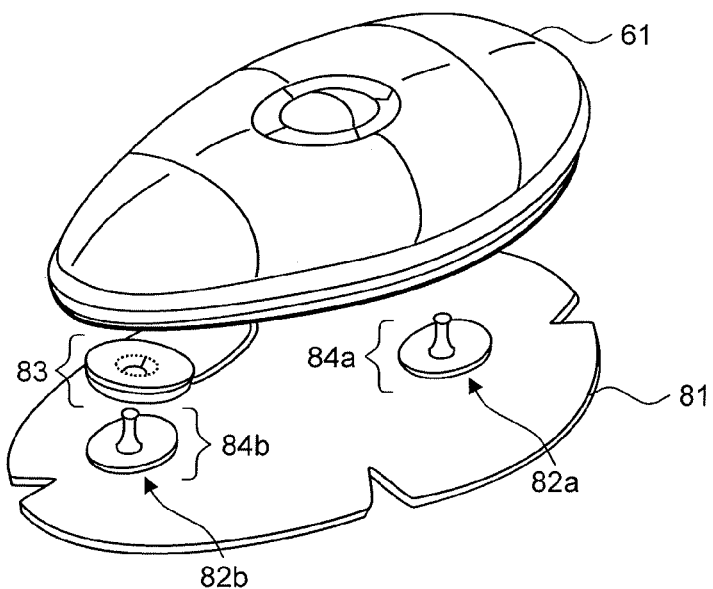
FIG. 8 is a functional block diagram showing an ambulatory electrocardiographic monitor with a jumpered sensing electrode in accordance with a further embodiment.

Although the construction of the basic monitor 41 can accommodate a wide range of different body characteristics and physiques, the manner in which the skin adhesive layer 46 is independently suspended can be further untied from the housing 61 to fit sharply sculpted or other difficult-to-adhese surfaces while permitting a wider range of motion. FIG. 8 is a functional block diagram showing an ambulatory electrocardiographic monitor 80 with a jumpered sensing electrode in accordance with a further embodiment. A pair of sensing electrodes 82*a-b* are mounted on opposite ends of a flexible and stretchable electrode mounting panel 81. Each sensing electrode 82*a-b* includes an electrode pad (not shown) facing the skin contacting surface of the electrode mounting panel 81. Each electrode pad is slightly recessed away from the skin contacting surface of the electrode mounting panel 81 and snuggly positioned between the electrode connection plug 84*a-b* and the electrode mounting panel 81. A layer of electrode gel is provided on the skin contacting surface of each electrode pad. Each sensing electrode 82*a-b* also includes an electrode connection plug 84*a-b* facing in the opposite direction towards the bottom of the housing 61. One or both of the electrodes 82*a-b* can be "jumpered," that is, connected by use of a jumper wire 83, which spans the space between the bottom of the housing 61 and the electrode mounting panel 81.

Figure 9:
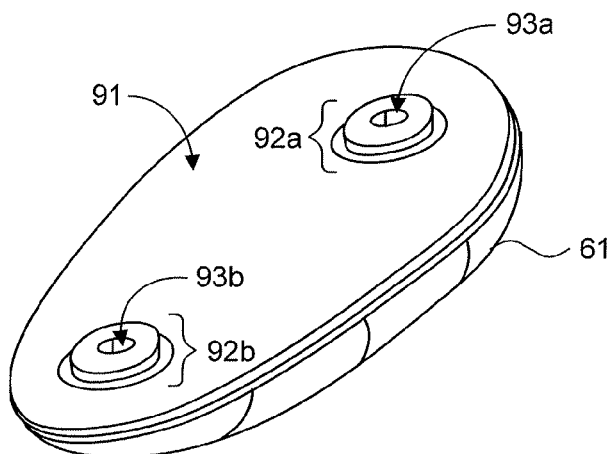
FIG. 9 is a functional block diagram showing the underside of the housing of the ambulatory electrocardiographic monitor of FIG. 8.

The jumper wire 83 electrically connects an electrode 84*a-b* to the circuitry on the PCB 43 (shown in FIG. 3), while also allowing that electrode 84*a-b* to physically float freely from the housing 61. FIG. 9 is a functional block diagram showing the underside 90 of the housing 61 of the ambulatory electrocardiographic monitor 80 of FIG. 8. On the bottom 91 of the housing 61, a pair of electrode connection receptacles 92*a-b* are provided. Each of the receptacles 92*a-b* respectively include a female receptacle 93*a-b* into which a corresponding electrode connection plug 84*a-b* be securely fit.

Figure 10:
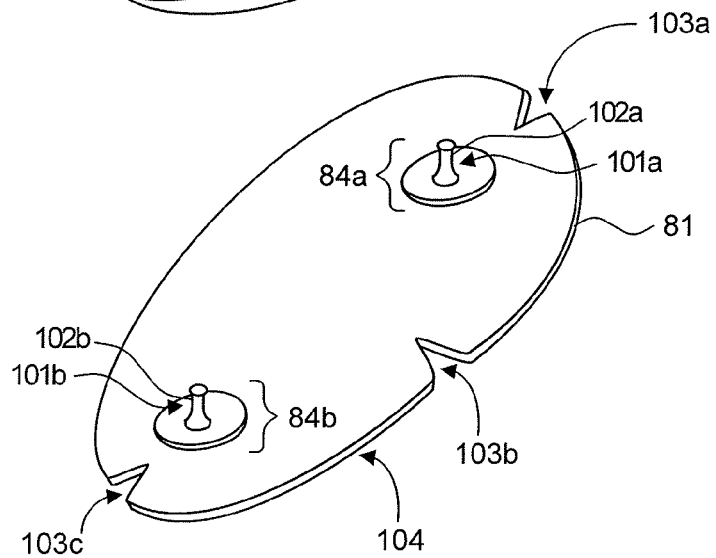
FIG. 10 is a functional block diagram showing the topside of the electrode mounting panel of the ambulatory electrocardiographic monitor of FIG. 8.

The configuration of the basic monitor 41 can be provided by coupling both of the electrode connection plugs 84*a-b* into the pair of electrode connection receptacles 92*a-b* on the bottom 91 of the housing 61. FIG. 10 is a functional block diagram showing the topside 100 of the electrode mounting panel 81 of the ambulatory electrocardiographic monitor 80 of FIG. 8. Each electrode mounting panel 81 includes a layer of skin adhesive 103 on a skin contacting surface. In a yet further embodiment, the electrode mounting panel 81 can include one or more triangular cutouts 103*a-c* or "darts" that are cut into the periphery of the adhesive pad 81 to more closely conform the adhesive pad 81 to an uneven or contoured skin surface.

In the basic monitor 41, described supra with reference to FIGS. 1-7, the electrode mounting panel 81 is independently suspended from the housing 61 through the mounting points of the electrode pairs 82a-b. Specifically, the electrode connection plugs 84a-b each include a groove 101 a-b defined circumferentially below a top section of a preferably round male stud 102a-b. The groove 101a-b enables the male stud 102a-b to securely engage a capture spring (not shown) positioned within each female receptacle 93a-b. The pairing of each electrode connection plug 84a-b and electrode connection receptacle 92a-b forms a "snap" connector, which enables the adhesive pad 81 to be removably fit into place, while still allowing the adhesive pad 81 to pivot independently from the housing 61. However, the maximal range of motion afforded to the electrode mounting panel 81 independent of the housing 61 proper is ultimately constrained by the degree to which the housing 61, particularly the enclosed PCB 43, and the electrode mounting panel 81 can flex and stretch.

Figure 11:
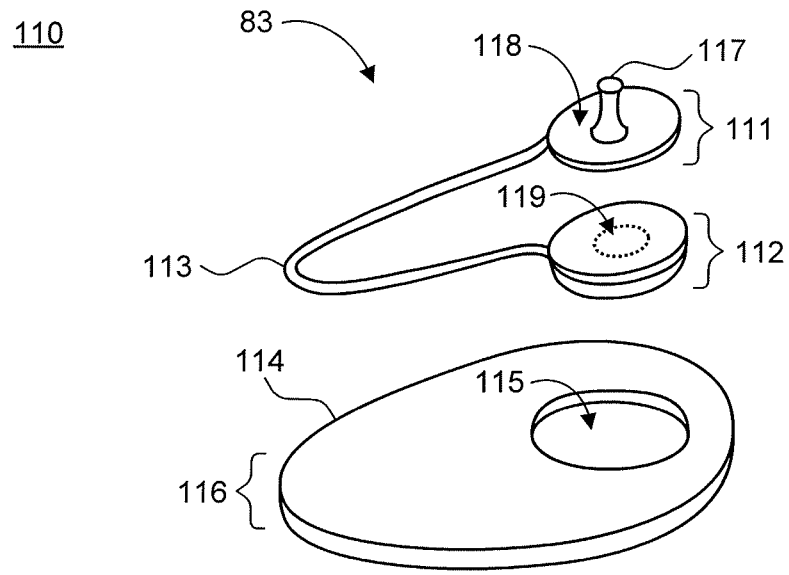
FIG. 11 is a functional block diagram showing the jumper wire of the ambulatory electrocardiographic monitor of FIG. 8.

Untying one or both of the electrodes 82a-b from a direct connection to the housing 61 can allow one or both ends of the electrode mounting panel 81 to float and move freely. FIG. 11 is a functional block diagram showing the jumper wire 83 of the ambulatory electrocardiographic monitor 80 of FIG. 8. The jumper wire 83 includes a jumper connection plug 111 on one end and a jumper connection receptacle 112 on the other end. The two ends are electrically connected by at least one electrically conductive and pliable wire 113. The jumper connection plug 111 includes a male stud 117 that can be securely fit into one of the electrode connection receptacles 92a-b on the bottom 91 of the housing 61. Similarly, the jumper connection receptacle 112 includes a female receptacle 119 over which one of the electrode connection plugs 84a-b on the electrode mounting panel 81 can be securely fit. Other manner of providing a jumpered interconnection between an electrode and the circuitry within the housing 61 are possible.

To help compensate for the inward angle of the body of the sternum past the fourth intercostal space 27 (shown in FIG. 2), especially in women, a standoff pad 114 can be used to create additional spacing 116 between the bottom 91 of the housing 61 and the electrode mounting panel 81. The standoff pad 114 is placed on one end of the housing 61 over one of the electrode connection receptacles 92a-b. The standoff pad 114 is sized smaller than the electrode mounting panel 81 and has at least one opening 115 for the electrode connection receptacle 92a-b.

Figure 12:
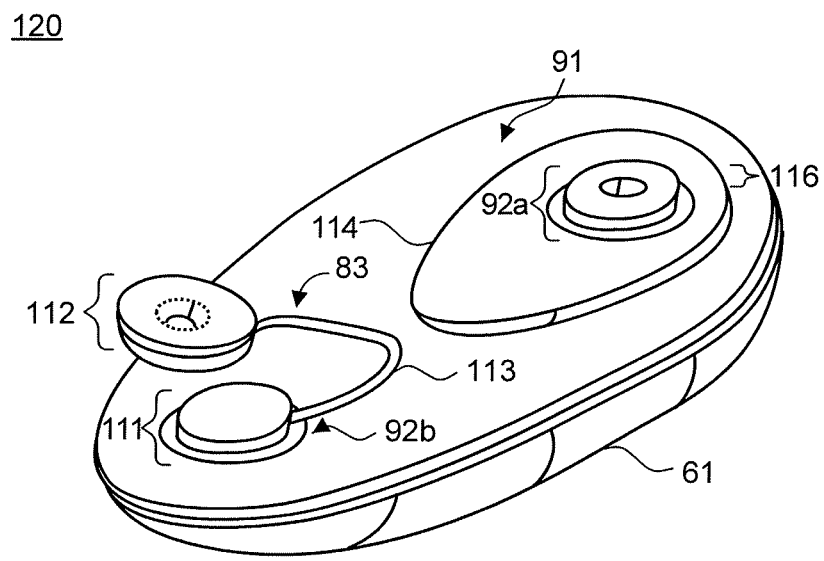
FIG. 12 is a functional block diagram showing the underside of the housing of the ambulatory electrocardiographic monitor of FIG. 8 with jumper wire attached.

The jumper wire 83 and the standoff pad 114, can be combined with the housing 61 to further independently suspend the electrode mounting panel 81 from the housing 61. FIG. 12 is a functional block diagram showing the underside of the housing 61 of the ambulatory electrocardiographic monitor 80 of FIG. 8 with jumper wire 83 attached. On one end of the housing 61, the jumper connection plug 111 is securely fit into one of the electrode connection receptacles 92a-b provided on the bottom 91 of the housing 61. The jumper connection receptacle 112 is likewise securely fit over one of the electrode connection plugs 84a-b mounted on the electrode mounting panel 81 (not shown). On the other end of the housing 61, the standoff pad 114 is placed on the bottom 81 of the housing 61 with the opening 115 approximately centered over one of the electrode connection receptacles 92a-b. The remaining electrode connection plug 84a-b on the electrode mounting panel 81 is securely fit into the electrode connection receptacle 92a-b. Thus, a spacing 116 is formed between the bottom 91 of the housing 61 and the electrode mounting panel 81 on the end of the housing 61 opposite from which the standoff pad 114 is placed to allow increased independent movement of the other end of the electrode mounting panel 81.

The jumper wire 83 allows untying of one end of the electrode mounting panel 81 from the bottom 91 of the housing 61. Alternatively, the electrical wiring connecting an electrode connection receptacle 92a-b on the housing 61 to an electrode connection plug 84a-b on the electrode mounting panel 81 could be formed integrally to the electrode mounting panel 81 proper. FIG. 13 is a functional block diagram showing an ambulatory electrocardiographic monitor 130 with hinged sensing electrode mounting panel 131 in accordance with a further embodiment. The electrode mounting panel 131 is functionally divided into three sections, an upper panel 132, a hinged portion 134 at one end of the upper panel 132, and a lower panel 133 folded under the upper panel 132. A standoff pad 132, such as described supra with reference to FIG. 11, is placed on the lower panel 133 to create a spacing 137 between the bottom of the housing 61 and the electrode mounting panel 131 to help compensate for the inward angle of the sternum, especially in women. The standoff pad 132 is placed over one of the electrode connection plugs 141a-b with the electrode connection plug positioned within the opening. As well, the upper panel 132 and lower panel 133 are hinged proximally to the standoff pad 132. The lower panel 132 includes a layer of skin adhesive 103 on a skin contacting surface. In addition, a pair of electrode pads 138a-b is mounted on the lower panel 132, approximately centered within openings 139a-b or "gel wells" defined around the electrode pads 138a-b and slightly recessed away from the skin contacting surface.

The upper panel 132 is electrically and physically coupled to the underside of the housing 61. FIG. 14 is a functional block diagram showing the electrode mounting panel 131 and the underside of the housing 61 of the ambulatory electrocardiographic monitor 130 of FIG. 13. A pair of electrode connection plugs 141a-b, is mounted on the upper panel 132 and securely fit into a corresponding pair of electrode connection receptacles 143a-b provided on the bottom of the housing 61. In a further embodiment, a handle 144 is formed on one end of the housing 61 to assist with unsnapping and removal of the housing 61 from the electrode mounting panel 131. The pairing of each electrode connection plug 141a-b and electrode connection receptacle 143a-b forms a "snap" connector, which enables the adhesive pad 131 to be removably fit into place, while still allowing the upper panel 132 of the adhesive pad 131 to pivot independently from the housing 61. Also, the openings 139a-b above the electrode pads 138a-b (not shown) are preferably filled with a conductive gel 142a-b on the skin contacting surface to facilitate signal conduction between the skin and the electrode pads 138a-b. In a yet further embodiment, the lower panel 133 of the electrode mounting panel 131 can include one or more triangular cutouts 144a-b or "darts" that are cut into the periphery of the lower panel 133 to more closely conform to an uneven or contoured skin surface.

Figure 15:
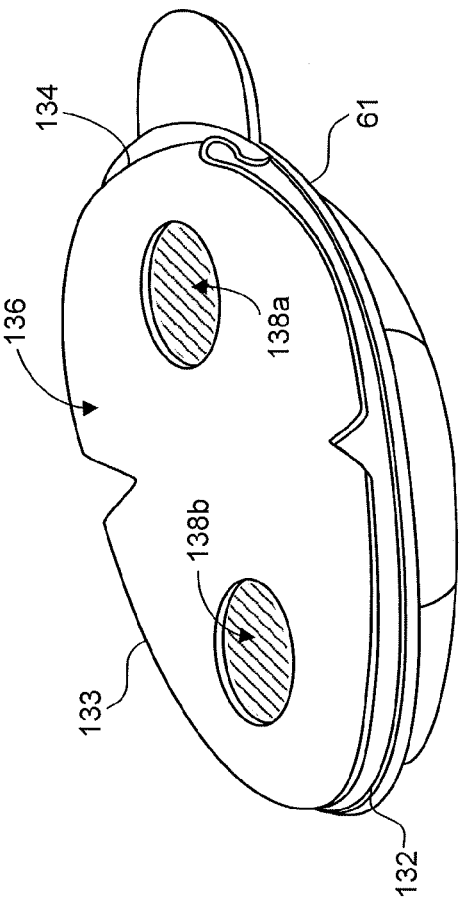
FIG. 15 is a functional block diagram showing the ambulatory electrocardiographic monitor of FIG. 13 with the electrode mounting panel folded over and assembled into place.

Each of the electrode connection plugs 141 a-b is electrically connected to a corresponding electrode pads 138a-b. FIG. 15 is a functional block diagram showing the ambulatory electrocardiographic monitor 130 of FIG. 13 with the electrode mounting panel 131 folded over and assembled into place. The upper panel 132 is attached to the housing 61 by securely engaging the pair of electrode connection plugs 141a-b (not shown) into a corresponding pair of electrode connection receptacles 143a-b (not shown) on the underside of the housing 61. The lower panel 133 is folded under the upper panel 132 at the hinged portion 134, which can be placed anywhere along the periphery of the upper panel 132 and lower panel 133. Additionally, in one embodiment, the electrode mounting panel 131 includes an integrated flexible circuit board with circuit traces electrically interconnecting the respective electrode connection plugs 141 *a-b* and electrode pads 138*a-b*. In a further embodiment, a set of wires electrically connect those components. The ability of the lower panel 133 to pivot from the upper panel 132 by virtue of the hinged portion 134 in combination with the spacing 137 formed between the underside of the housing 61 and the lower panel 133 on the end opposite from which the standoff pad 135 is placed allows increased independent movement of the other end of the lower panel 133. Other manner of providing an integrated and suspended interconnection between an electrode and the circuitry within the housing 61 are possible.

Figure 16:
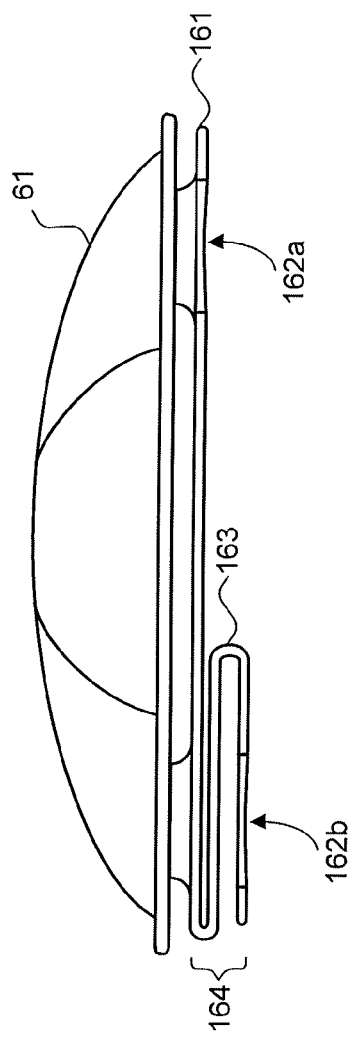
FIG. 16 is a functional block diagram showing a side view of an ambulatory electrocardiographic monitor with extendable sensing electrode mounting panel in accordance with a further embodiment.

Ordinarily, the spacing between the two sensing electrodes on the electrode mounting panel is fixed. The signal strength achievable with standard spacing inter-electrode may be adversely diminished in women, especially active or large breasted, buxom women, as well as in excessively large or obese patients, male or female. FIG. 16 is a functional block diagram showing a side view of an ambulatory electrocardiographic monitor 160 with extendable electrode mounting panel 161 in accordance with a further embodiment. The inter-electrode spacing can be made adjustable by including an accordion-like folded extension panel. Increasing the spacing allows better signal reception and lower noise. The electrode mounting panel 161 includes an extension panel 163, which has several collapsible folds 164 that are provided in-between the extension panel 163 and the electrode mounting panel 161 proper. The electrode mounting panel 161 is attached to the housing 61 by securely engaging a pair of electrode connection plugs (not shown) mounted on the housing facing surface of the electrode mounting panel 161 into a corresponding pair of electrode connection receptacles (not shown) on the underside of the housing 61. Additionally, the electrode mounting pad 161 is separated from the housing by set of standoffs 165*a-b* having non-uniform heights, which are affixed to and define an increasingly wide gap between the electrode mounting pad 161 and a bottom surface of the housing 61, to help compensate for the inward angle of the sternum, especially in women. Additionally, in one embodiment, the electrode mounting panel 161 includes an integrated flexible circuit board with circuit traces electrically interconnecting the electrode connection plugs and the electrodes pads 162*a-b*. In a further embodiment, a set of wires electrically connect those components. Finally, a standoff pad (not shown) can be used to create additional spacing between the bottom of the housing 61 and the electrode mounting panel 161.

Figure 17:
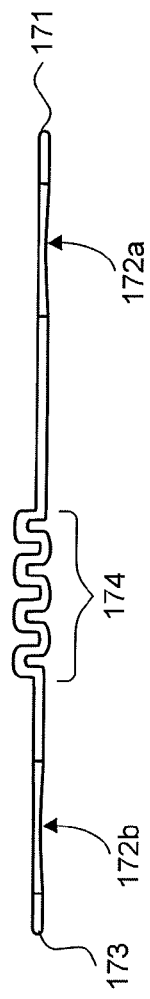
FIG. 17 is a functional block diagram showing a side view of an extendable electrode mounting panel in accordance with a still further embodiment.

The extension panel can be provided in other configurations. FIG. 17 is a functional block diagram showing a side view of an extendable electrode mounting panel 171 in accordance with a still further embodiment. Rather than folding the extension panel in-between the housing and the electrode mounting panel, the electrode mounting panel 161 itself has several collapsible folds 174 that are provided in-line between the pair of electrode pads 172*a-b*. In addition, the extension panel could be elasticized between the pair of electrode pads 172*a-b* to stretch in-line with and outward from the electrode pads 172*a-b*. Other manner of allowing the electrode mounting panel 161 to be extended are possible.

Figure 18:
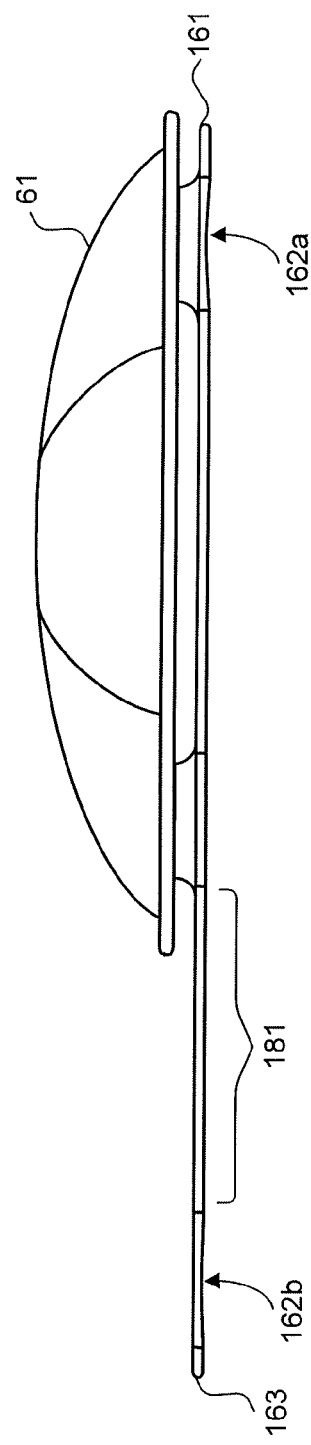
FIG. 18 is a functional block diagram showing a side view of the ambulatory electrocardiographic monitor of FIG. 16 with the electrode mounting panel extended.
Figure 19:
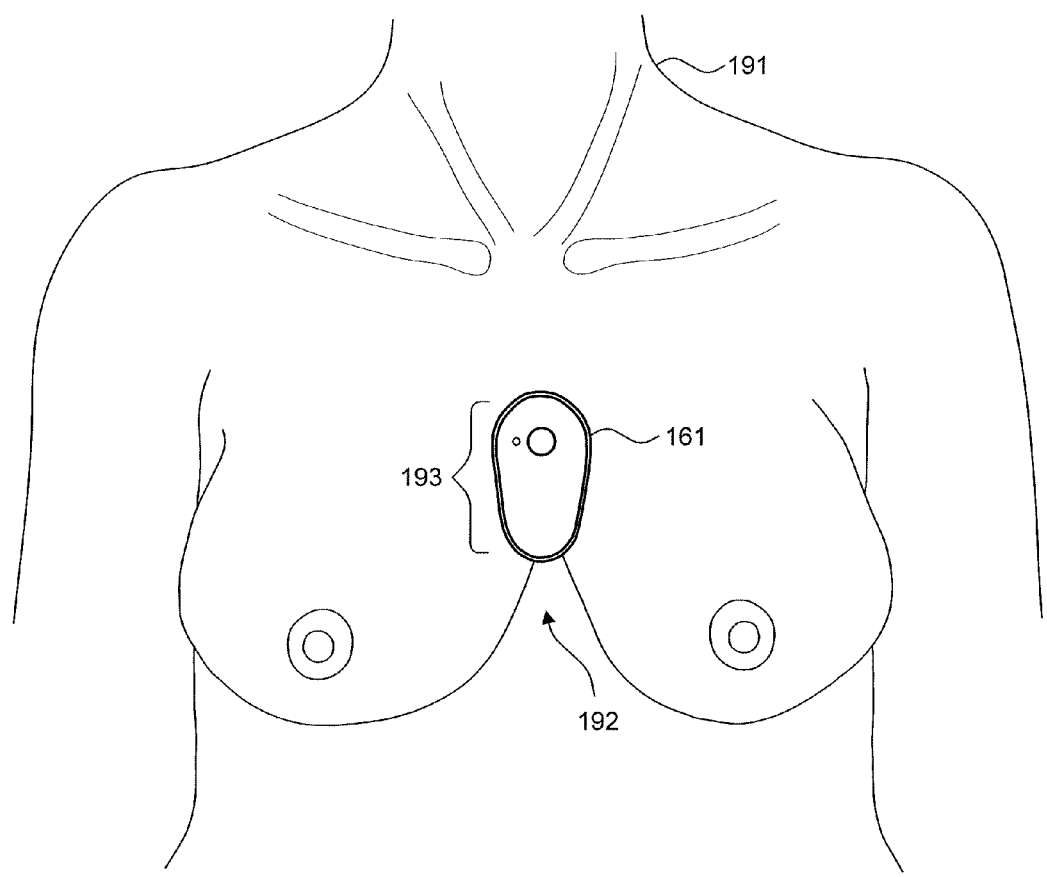
FIGS. 19 and 20 are front anatomical diagrams respectively showing placement of the ambulatory electrocardiographic monitor of FIG. 16 on a female patient with the electrode mounting panel folded and extended.
Figure 20:
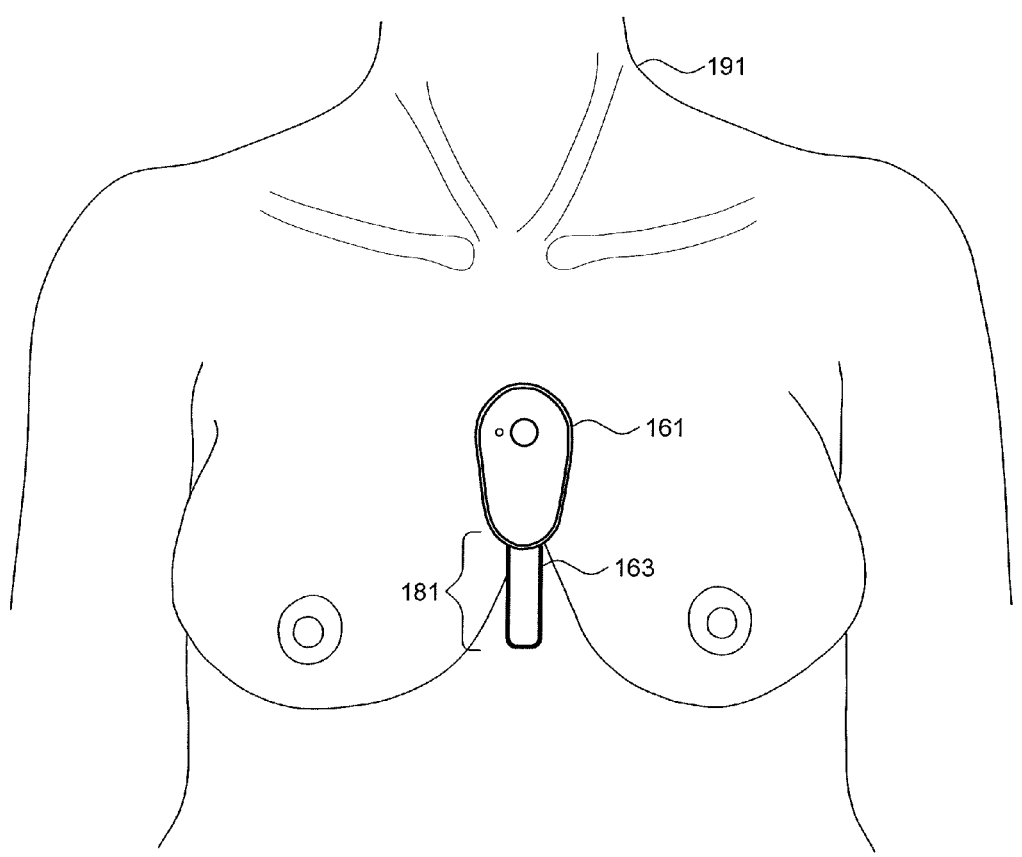

The spacing between the two sensing electrodes can be extended when necessary to increase the distance between the sensing electrodes. FIG. 18 is a functional block diagram showing a side view of the ambulatory electrocardiographic monitor 160 of FIG. 16 with the electrode mounting panel 161 extended. The distance between the pair of electrodes pads 172*a-b* can be extended by laterally urging the extension panel 163 of the electrode mounting panel 161 outwards and away from the housing 61. The inter-electrode distance can be increased up to the maximal extension 181 of the collapsible folds 164 (not shown), although the full amount of extension may not be required in every case. FIGS. 19 and 20 are front anatomical diagrams 190, 200 respectively showing placement of the ambulatory electrocardiographic monitor 160 of FIG. 16 on a female patient 191 with the electrode mounting panel 161 folded and extended. Initially, the monitor 160 is positioned between the breasts 192 on the sternum 192 at a point located between the suprasternal notch and manubrium, as further described supra. If signal quality is poor due to patient-related factors, such as obesity or bone mass, the extension panel 163 of the electrode mounting panel 161 can be extended outwards and away from the housing 61 to increase the spacing between the sensing electrodes, thereby lowering impedance and improving signal quality. In one embodiment, the extension panel 163 enables the inter-electrode spacing to be increased up to an additional 3 cm, although other lengths of increased spacing are possible.

Figure 21:
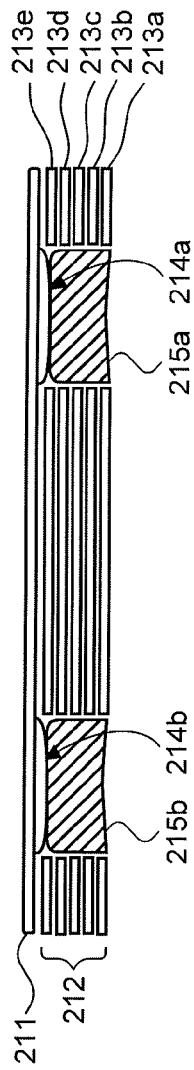
FIG. 21 is a functional block diagram showing a side view of an ambulatory electrocardiographic monitor with an incrementally disposable sensing electrode mounting panel in accordance with a further embodiment.

To facilitate overall long term monitoring through a series of short term monitoring periods, a stack of peel-away layers of disposable skin adhesive pads can be provided. FIG. 21 is a functional block diagram showing a side view of an ambulatory electrocardiographic monitor 210 with an incrementally disposable electrode mounting panel 212 in accordance with a further embodiment. The incrementally disposable electrode mounting panel 212 includes a base layer 211 upon opposite sides of which a pair of sensing electrodes 214*a-b* are mounted. A plurality of peel-away layers 213*a-e* are then applied to the base layer 211. Each peel-away layer 213*a-e* includes a skin adhesive on one side and a backing on the other side. The peel-away layers 213*a-e* are successively stacked, with the backing of each outermost layer placed against the skin adhesive of the next innermost layer. The peel-away layers 213*a-e* are independently suspended from the housing 61 of an ambulatory monitor, such as described above with reference to FIGS. 1-7, with a set of standoffs (not shown) having non-uniform heights affixed to and defining an increasingly wide gap between the skin adhesive layer and a bottom surface of the housing.

When in use, the skin adhesive of the outermost peel-away layer is initially exposed to allow the monitor 210 to be placed on a patient by a physician or other caregiver. The patient can be instructed on proper placement of the monitor 210. Thereafter, the patient can remove the monitor 210 as needed to permit cleaning and to allow revitalization of the underlying skin. When ready, the patient can then peel off the outermost layer of the electrode mounting panel 212 and expose the fresh skin adhesive of the next innermost layer prior to replacing the monitor 210 on his or her sternum.

Figure 22:
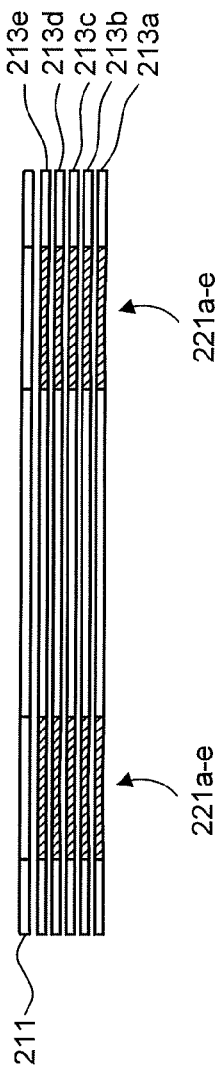
FIG. 22 is a functional block diagram showing a side view of an ambulatory electrocardiographic monitor with an incrementally disposable sensing electrode mounting panel in accordance with a still further embodiment.

Each peel-away layer 213*a-e* defines a pair of holes that fit over the sensing electrodes 214*a-b*. When all of the peel-away layers 213*a-e* are stacked, the pairs of holes form a set of holes 215*a-b* or "gel wells" on the skin contacting surface of the electrode mounting panel 212 into which conductive gel can be placed. However, as the number of peel-away layers 213*a-e* increases, the distance between each electrode pad and the skin surface also increases. FIG. 22 is a functional block diagram showing a side view of an ambulatory electrocardiographic monitor 220 with an incrementally disposable electrode mounting panel 211 in accordance with a still further embodiment. A plurality of peel-away layers is again provided, but each layer also includes a disposable electrode pad 221a-e, which is discarded with each peeled off layer. Other manner of providing peel-away disposable electrode pad convenience is possible.

While the invention has been particularly shown and described as referenced to the embodiments thereof, those skilled in the art will understand that the foregoing and other changes in form and detail may be made therein without departing from the spirit and scope.

What is claimed is:

1. An ambulatory electrocardiographic (ECG) monitor with hinged sensing electrode mounting panel, comprising: self-powered ECG sensing circuitry; a housing fully enclosing the sensing circuitry and providing a pair of electrode connection receptacles on a bottom surface of the housing; and a flexible and stretchable electrode mounting panel, comprising: an upper panel facing the bottom surface of the housing and a lower panel hingably folded under the upper panel and having an elongated shape which is proximal to standoff pads; wherein the standoff pads are comprised of greater height affixed at opposite ends of the bottom surface of the housing than the standoff pad comprised of a lesser height; a layer of skin adhesive on a skin contacting surface; a standoff pad sized smaller than the electrode mounting panel and defining an opening; a pair of sensing electrodes mounted on opposite ends of the lower panel and comprising an electrode pad facing the skin contacting surface, wherein the standoff pad is placed over one of the sensing electrodes with the electrode connection plug positioned within the opening and the upper panel and lower panel are hinged proximally to the standoff pad; and a pair of electrode connection plugs removably and pivotably couplable into the electrode connection receptacles on the housing, each connection plug electrically connected to one of the sensing electrodes.

2. A monitor according to claim 1, further comprising one of:
    a flexible circuit board integrated into the electrode mounting panel and comprising circuit traces electrically interconnecting the respective electrode connection plugs and sensing electrodes; and
    a set of wires electrically connecting the respective electrode connection receptacles and the sensing electrodes.

3. A monitor according to claim 1, further comprising:
    a layer of electrode gel provided on the skin contacting surface of each sensing electrode, wherein the electrode pad slightly is recessed away from the skin contacting surface and is snuggly positioned between the electrode connection plug and the electrode mounting panel.

4. A monitor according to claim 1, wherein a portion of the lower panel between the sensing electrodes comprises one or more collapsible folds.

5. A monitor according to claim 1, wherein the skin adhesive comprises at least one of a single-coated silicon adhesive gel and an elastomer film.

6. A monitor according to claim 1, wherein the electrode mounting panel is further sized to fit between a patient's suprasternal notch and manubrium.

7. An ambulatory electrocardiographic (ECG) monitor with extendable sensing electrode mounting panel, comprising: self-powered ECG sensing circuitry; a housing fully enclosing the sensing circuitry and providing a pair of electrode connection receptacles on a bottom surface of the housing; a flexible and stretchable electrode mounting panel having an elongated shape, comprising: an extension panel collapsibly provided on one side of the electrode mounting panel; a layer of skin adhesive on a skin contacting surface of each of the electrode mounting panel and the extension panel, the skin adhesive layer independently suspended from the housing with a set of standoffs having non-uniform heights affixed to and defining an increasingly wide gap between the skin adhesive layer and a bottom surface of the housing, wherein the standoffs are comprised of greater height affixed at opposite ends of the bottom surface of the housing than the standoffs comprised of a lesser height; and a portion of the extension panel further comprising at least one of: one or more collapsible folds provided in-line with the extension panel and the electrode mounting panel; one or more collapsible folds provided between the extension panel and the electrode mounting panel; and an elasticized panel stretching in-line with and provided between the extension panel and the electrode mounting panel; and a pair of sensing electrodes with one sensing electrode mounted on the extension panel and the other sensing electrode mounted on the electrode mounting panel distally from the extension panel-mounted sensing electrode, each sensing electrode comprising an electrode pad facing the skin contacting surface and an oppositely-facing electrode connection plug, the electrode connection plugs removably and pivotably couplable into the electrode connection receptacles on the housing.

8. A monitor according to claim 7, further comprising:
    a standoff pad sized smaller than the electrode mounting panel and defining an opening, wherein the standoff pad is placed over one of the sensing electrodes with the electrode connection plug positioned within the opening.

9. A monitor according to claim 7, further comprising one of:
    a flexible circuit board integrated into the electrode mounting panel and comprising circuit traces electrically interconnecting the respective electrode connection plugs and sensing electrodes; and
    a set of wires electrically connecting the respective electrode connection receptacles and the sensing electrodes.

10. A monitor according to claim 7, further comprising:
    a layer of electrode gel provided on the skin contacting surface of each sensing electrode, wherein the electrode pad slightly is recessed away from the skin contacting surface and is snuggly positioned between the electrode connection plug and the electrode mounting panel.

11. A monitor according to claim 7, wherein the skin adhesive comprises at least one of a single-coated silicon adhesive gel and an elastomer film.

12. A monitor according to claim 7, wherein the electrode mounting panel is further sized to fit between a patient's suprasternal notch and manubrium.

13. An ambulatory electrocardiographic (ECG) monitor with an incrementally disposable sensing electrode mounting panel, comprising: self-powered ECG sensing circuitry; a housing fully enclosing the sensing circuitry and providing a pair of electrode connection receptacles on a bottom surface of the housing: a flexible and stretchable electrode mounting panel having an elongated shape, comprising: a plurality of peel-away layers, which each comprise skin adhesive and a backing on an oppositely-facing surface, the peel-away layers successively stacked with backing to skin adhesive, an outermost peel-away layer exposing the skin adhesive on a skin contacting surface of the electrode mounting panel, the peel-away layers independently suspended from the housing with a set of standoffs having non-uniform heights affixed to and defining an increasingly wide gap between the skin adhesive layer and a bottom surface of the housing; housing, wherein the standoffs are comprised of greater height affixed at opposite ends of the bottom surface of the housing than the standoffs comprised of lesser height; and a pair of sensing electrodes mounted on the electrode mounting panel, wherein the electrode mounting panel further comprises: a base layer comprising a skin adhesive on a skin contacting surface and upon which an innermost peel-away layer is removable adhered, wherein the sensing electrodes are mounted on the base layer; and a layer of electrode gel provided on the skin contacting surface of each sensing electrode, the electrode pad being slightly recessed away from the skin contacting surface and snuggly positioned between the electrode connection plug and the electrode mounting panel, a plurality of pairs of peel-away electrode pad surfaces, each comprised on one of the peel-away layers and successively stacked in electrical communication, one against the other from the outermost peel-away layer in; each sensing electrode comprising an electrode pad facing the skin contacting surface and an oppositely-facing electrode connection plug, the electrode connection plugs removably and pivotably couplable into the electrode connection receptacles on the housing.

14. A monitor according to claim 13, wherein the electrode mounting panel is further sized to fit between a patient's suprasternal notch and manubrium.

15. A monitor according to claim 13, wherein the skin adhesive comprises at least one of a single-coated silicon adhesive gel and an elastomer film.

16. A monitor according to claim 13, wherein the electrode mounting panel is further sized to fit between a patient's suprasternal notch and manubrium.

\* \* \* \* \*